United States Patent
Ohmiya et al.

(10) Patent No.: US 8,343,729 B2
(45) Date of Patent: Jan. 1, 2013

(54) LUCIFERIN LUMINESCENT SUBSTRATE OF MARINE OSTRACOD CRUSTACEAN AND METHOD FOR PRODUCTION THEREOF

(75) Inventors: Yoshihiro Ohmiya, Ikeda (JP); Chun Wu, Ikeda (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 13/067,565

(22) Filed: Jun. 9, 2011

(65) Prior Publication Data
US 2011/0287459 A1 Nov. 24, 2011

Related U.S. Application Data

(62) Division of application No. 11/992,660, filed as application No. PCT/JP2006/319000 on Sep. 25, 2006, now Pat. No. 7,989,621.

(30) Foreign Application Priority Data

| | | |
|---|---|---|
| Sep. 26, 2005 | (JP) | 2005-277020 |
| Feb. 1, 2006 | (JP) | 2006-24176 |
| Mar. 17, 2006 | (JP) | 2006-73818 |
| May 9, 2006 | (JP) | 2006-130203 |

(51) Int. Cl.
*C12Q 1/58* (2006.01)
*C07D 491/00* (2006.01)
*C07D 495/00* (2006.01)
*C07D 497/00* (2006.01)

(52) U.S. Cl. .......................... 435/8; 544/350

(58) Field of Classification Search .................. 435/8
See application file for complete search history.

(56) References Cited

U.S. PATENT DOCUMENTS

| | | | |
|---|---|---|---|
| 5,518,883 A | 5/1996 | Soini | |
| 5,783,382 A | 7/1998 | Aoyama et al. | |
| 6,152,358 A | 11/2000 | Bryan | |
| 7,718,389 B2 * | 5/2010 | Ohmiya et al. | 435/8 |

FOREIGN PATENT DOCUMENTS

| | | |
|---|---|---|
| EP | 0955497 A1 | 11/1999 |
| JP | 03-030678 | 2/1991 |
| JP | 05-060697 | 3/1993 |
| JP | 05-286976 | 11/1993 |
| JP | 7-502820 | 3/1995 |
| JP | 9-201397 | 8/1997 |
| JP | 11-504822 | 5/1999 |
| JP | 2004-187652 | 7/2004 |
| JP | 2005-169768 | 6/2005 |
| WO | WO 90/01542 | 2/1990 |
| WO | WO 2004/052934 | 6/2004 |

OTHER PUBLICATIONS

Kropec A, Huebner J, Frank U, Lemmen S, Hirt U, Daschner FD. In vitro activity of sodium bisulfite and heparin against staphylococci: new strategies in the treatment of catheter-related infection. J Infect Dis. Jul. 1993;168(1):235-7.*

Rees JF, de Wergifosse B, Noiset O, Dubuisson M, Janssens B, Thompson EM. The origins of marine bioluminescence: turning oxygen defence mechanisms into deep-sea communication tools. J Exp Biol. Apr. 1998;201(Pt 8):1211-21.*

Thompson et al., "Induction of Bioluminescence Capability in the Marine Fish, *Porichthys Notatus*, by *Vargula* (*Crustacean*) [14C]Luciferin and Unlabelled Analogues", *The Journal of Experimental Biology*, 137; 39-51, 1988.

Adamczyk et al., "A Convenient Method for the Preparation of α-Ketoacetals", *Synthetic Communications*, 32/20, 2002.

De Kimpe et al., "Reactivity of Primary and Secondary N-2-(1,1-Dichloroalkylidene)anilines, V[1,2]"; *The Journal of Organic Chemistry*, 40/25, 3749-3756, 1975.

Sassa, "Structure and Absolute Configuration of Macrophoma Fruit Rot Toxin A", *Agricultural and Biological Chemistry*, 47; 1417-1418, 1983.

Thompson et al., "*Vargula hilgendorfii* luciferase: a secreted reporter enzyme for monitoring gene expression in mammalian cells", *Gene*, 96, 257-262, 1990.

Nakajima et al., "cDNA Cloning and Characterization of a Secreted Luciferase from the Luminous Japanese Ostracod, *Cypridina noctiluca*", *Biosci. Biotechnol. Biochem.*, 68; 565-570, 2004.

Inouye et al., "Imaging of luciferase secretion from transformed Chinese hamster ovary cells", *Proc. Natl. Acad. Sci. USA*, 89, 9584-9587, 1992.

Tanahashi et al., "Continuous Measurement of Targeted Promoter Activity by a Secreted Bioluminescence Reporter, *Vargula hilgendorfii* Luciferase", *Analytical Biochemistry*, 289, 260-266, 2001.

Kishi et al., "Cypridina Bioluminescence III Total Synthesis of *Cypridina* Luciferin", *Tetrahedron Letters*, No. 29, 3445-3450, 1966.

Karpetsky et al., "An Unambiguous Synthesis of *Cypridina* Etioluciferamine. An Application of Titanium Tetrachloride to the Synthesis of Pyrazine *N*-Oxides", *Journal of American Chemical Society*, 93:90, 2333-2335, 1971.

Nakamura et al., "Convergent and short-step syntheses of *dl*-Cypridina luciferin and its analogues based on Pd-mediated cross couplings", *Tetrahedron Letters*, 41, 2185-2188, 2000.

Toya, "Umi Hotaru Seibutsu Hakko no Kagaku", *Nippoin Nogei Kagaku Kaish*, 66, No. 4, 742-747, 1992.

Baganz H., and Hans-Joachim May, "Reaktionen von α-Diazocarbonyl-Verbindungen mit tert.-Butylhypochlorit", *Chemische Berichte, Verlag Chemie GmbH., Weihheim, DE*, vol. 99, Jan. 1, 1966, pp. 3766-3770.

Wiberg, Kenneth B., and Thomas W. Hutton, "The Stereochemistry of the Wolff Rearrangement", *J. Am. Chem. Society*, vol. 78, No. 8, Apr. 20, 1956, pp. 1640-1645.

Aoyama, Toyohiko, and Takayuki Shioiri, "New Methods and Reagents in Organic Synthesis. 8. Trimethylsil Yldiaszomethanel. A new, Stable, and Safe Reagent for the Classical Arndt-Eistert Synthesis", *Tetrahedron Letters*, vol. 21, No. 46, 1980, pp. 4461-4462.

Wu, Chun, et al. "Syntheses and evaluation of the bioluminescent activity of (S)-Cypridina luciferin and its analogs", Tetrahedron Letters, vol. 47, No. 5, Jan. 30, 2006, pp. 753-756.

Supplementary European Search Report dated Mar. 3, 2010.

S. Sugiura et al.; "Synthesis of Cypridina Luciferin and Related Compounds. VIII. Improvement in the Synthesis of Cypridina Luciferin"; Yakugaku Zasshi, 90 (6); 1970; pp. 707-710.

S. Inoue et al.; "Cypridina Bioluminescence VI a New Route for the Synthesis of Cypridina Luciferin and its Analogs"; *Tetrahedron Letters*; No. 20; 1969; pp. 1609-1610.

Y. Toya et al.; "Synthesis and Chemiluminescence Properties of 6-(4-Methoxyphenyl)-2-methylimidazo[1,2-α]-pyrazin-3(7*H*)-one and 2-Methyl-6-(2-naphthyl)-imidazo[1,2-α]pyrazin-3(7*H*)-one"; *Bulletin of the Chemical Society of Japan*; 65 (9); 1992; pp. 2475-2479.

C. Wu et al.; "Chemi- and bioluminescence of coelenterazine analogues with a conjugated group at the C-8 position"; *Tetrahedron Letters*; 42 (16); 2001; pp. 2997-3000.

Russell C. Hart et al.; "*Renilla reniformis* Bioluminescence: Luciferase-Catalyzed Production of Nonradiating Excited States from Luciferin Analogues and Elucidation of the Excited State Species Involved in Energy Transfer to Renilla Green Fluorescent Protein"; *Biochemistry*, 18 (11); 1979; pp. 2204-2210.

T. Hirano et al.; "Mass Spectrometric Studies on Chemiluminescence of Coelenterate Luciferin Analogues"; *Tetrahedron*; 49 (41); 1993; pp. 9267-9276.

Japanese Office Action mailed Apr. 5, 2011.

Goto, T. et al., "Cypridina Bioluminescence V. Structure of Emitting Species in the Luminescence of Cypridina Luciferin and its Related Compounds", *Tetrahedron Letters*, No. 37, pp. 4035-4038, 1968.

Kato, S. et al., "Identification of the biosynthetic units of Cypridina luciferin in *Cypridina* (*Vargula*) *hilgendorfii* by LC/ESI-TOF-MS", *Tetrahedron Letters*, 60 (2004), pp. 11427-11434.

Nakamura, H. et al., "Synthesis and Chemiluminescence of 5-[(2-Pyridyl)-, (2-Pyrazinyl)-, and (Substituted 2-pyrazinyl)amino]-1,2,4-trioxanes", *Bull. Chem. Jpn.*, vol. 61, No. 10, pp. 3776-3778 (1988).

Yoshito, K. et al., "Cypridina Bioluminescence I* Structure of *Cypridina* Luciferin", *Tetrahedron Letters*, No. 29, pp. 3427-3436, 1966.

U.S. Appl. No. 12/588,671, filed Oct. 23, 2009, Ohmiya et al.

A.M. Chase et al.. "Cypridina Luciferin Oxidation as a Function of pH, and Reduction of Luciferin by Ascorbic Acid", *Johns Hopkins University, McCollum-Pratt Institute*, Contribution No. 302: 258-261 (1961).

F.H. Johnson et al., "Action of Cyanide on Cypridina Luciferin", *Journal of Cellular and Comparative Physiology*, 59: 265-272 (1962).

\* cited by examiner

*Primary Examiner* — Paul Zarek

(74) *Attorney, Agent, or Firm* — Kratz, Quintos & Hanson, LLP

(57) ABSTRACT

The present invention relates to a method for producing marine ostracod crustacean luciferin or a derivative thereof represented by a general formula (4), characterized by reacting a compound represented by a general formula (2) with a compound represented by a general formula (3):

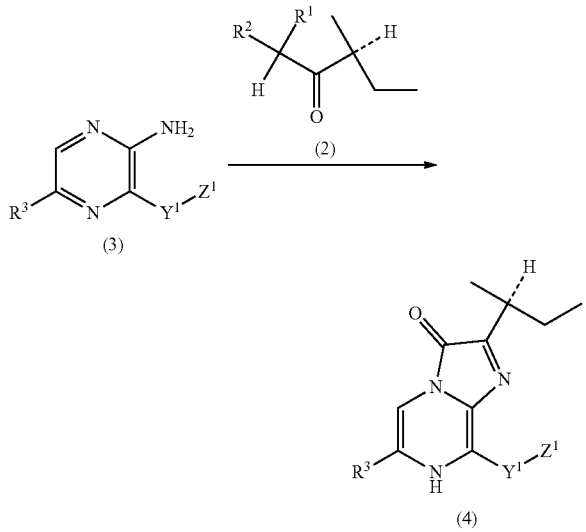

wherein $R^1$, $R^2$, $R^3$, $R^5$, $Y^1$ and $Z^1$ are the same as defined in the specification.

5 Claims, 4 Drawing Sheets

US 8,343,729 B2

LUCIFERIN LUMINESCENT SUBSTRATE OF MARINE OSTRACOD CRUSTACEAN AND METHOD FOR PRODUCTION THEREOF

CROSS-REFERENCE TO RELATED APPLICATION

This is a Divisional Application of U.S. patent application Ser. No. 11/992,660, filed on Mar. 25, 2008 now U.S. Pat. No. 7,989,621, which is a 371 National stage application of PCT/JP2006/319000, filed on Sep. 25, 2006, the prior applications being hereby incorporated by reference.

STATEMENT REGARDING FEDERALLY SPONSORED OR DEVELOPMENT

Not Applicable

THE NAMES OF PARTIES TO A JOINT RESEARCH AGREEMENT

Not Applicable

REFERENCE TO SEQUENCE LISTING

Not Applicable

BACKGROUND OF THE INVENTION

1. Technical Field

The present invention relates to a method for producing luciferin (luminescent substrate) which reacts with a marine ostracod crustacean luciferase, and a novel marine ostracod crustacean luciferin compound and establishment of a technology for producing the same.

The present invention also relates to a derivative having a different luminescence wavelength from that of natural marine ostracod crustacean luciferin, a derivative and a composition having a low background, and a method for measuring luminescence.

2. Background Art

Luminescent crustacea, marine ostracod crustacean and its related species have a secretory luminescent enzyme (luciferase) and a luminescent substrate (luciferin), and the luciferin of marine ostracod crustacean emits a blue light with a maximum luminescence wavelength of 460 nm by an oxidation reaction using the luciferase of marine ostracod crustacean as a catalyst.

Since the luciferase of marine ostracod crustacean is characterized by being secreted extracellularly, when a cloned cDNA is used as a reporter gene, a synthesized protein is secreted extracellularly in mammalian cells and yeast cells. Accordingly, a luminescence activity of marine ostracod crustacean luciferase can be measured without disrupting the cell, and thus, for example, a gene transcription activity in the mammalian cell can be measured extracellularly (Non-patent Literatures 1 to 2, Patent Documents 1 to 3). Marine ostracod crustacean luciferase has been also used as secretory luciferase for a reporter assay in the yeast cells (Patent Document 4).

In reports using this luminescent enzyme, an example in which the secretion of a protein from the cell was visualized by performing an image analysis of this secretory luminescent enzyme (Non-patent Literature 3) and an example in which a change of the transcription activity in living cells was continuously measured by using the mammalian cells in which a reporter gene of marine ostracod crustacean inserting a transcription activity region of a growth hormone gene had been introduced (Non-patent Literature 4) are available. An example in which processing of a peptide from a protein was quantified by a fusion body of marine ostracod crustacean luciferase and a fluorescent protein (Patent Document 5) is also available.

In the field of drug discovery, it is important to develop and search protein expression inhibitors and secretion inhibitors, and screenings have been performed using the change of the gene transcription activity of a target protein in the cell as an indicator. It is a role of the reporter gene (protein) to report the change of the gene transcription activity due to an effect of the inhibitor. As the reporter protein, it is required not only to report on/off of the gene but also to have properties, e.g., being capable of analyzing the change of inhibitor effects with time (high time resolution), the reporter protein by itself not having the inhibitory effect, or the reporter protein not disturbing intracellular functions (non-cytotoxicity). As the reporter gene accomplishing the high time resolution and having no cytotoxicity, the reporter protein produced in the cell is required to be rapidly secreted or metabolized.

Marine ostracod crustacean luciferase is secreted and the secreted luciferase can be used to rapidly measure the change of the transcription activity extracellularly. Thus, the range of its use is wide. Although marine ostracod crustacean luciferase is such a useful reporter enzyme, its practical application and general use have been given up. This is because there is a great problem that luciferin, a substrate of luciferase, is not sufficiently supplied.

Problematic issues of marine ostracod crustacean luciferin include difficulty of stable supply of luciferin, self-luminescence of marine ostracod crustacean luciferin with albumin protein, and its luminescence wavelength overlapped with other luminescence systems.

In all previously reported syntheses of marine ostracod crustacean luciferin, an intermediate is etioluciferin which is a precursor. The synthesis of etioluciferin minimally requires 7 steps (Non-patent Literatures 5 to 7). If a yield is poor in the final step from etioluciferin to marine ostracod crustacean luciferin, it is necessary to prepare a raw material in a large amount. Thus, a cost for producing luciferin is remarkably increased. According to a method described in the previous literature, the yield of optically active luciferin synthesized by a condensation reaction of 3-methyl-2-oxovaleric acid with etioluciferin is 2% in 3 steps (Non-patent Literature 5, FIG. 1). This way, the yield in the final step is extremely low. Thus, it is actually difficult to produce optically active marine ostracod crustacean luciferin by organic synthesis on a commercial basis.

Racemic luciferin (Non-patent Literature 7) exhibits only about a half activity of native luciferin and has a luminescence background of non-native luciferin not depending on luciferase. Thus it is an extremely important issue in bioassay to synthesize optically active luciferin.

Meanwhile, marine ostracod crustacean luciferin and *Renilla* luciferin have an imidazopyrazinone skeleton as a basic skeleton. Thus, their maximum luminescence wavelengths are close and around 460 to 480 nm although they are somewhat different due to their luciferase structures. Thus, it is difficult to simultaneously measure these two luminescence systems.

There is the example in which the processing the active peptide from the protein was quantified by the fusion body of marine ostracod crustacean luciferase and the fluorescent protein. Strokes shift between the luminescence maximum (460 nm) of marine ostracod crustacean luciferase and the fluorescence maximum (525 nm) of the fluorescent protein is small which was about 60 nm. Thus, it was observed that the luminescence of marine ostracod crustacean luciferase interfered with the fluorescence of the fluorescent protein. This light interference causes the high background in quantification of the processing of the peptide. Thus, it has been desired to develop marine ostracod crustacean luciferin analogs having the different maximum luminescence wavelength.

Furthermore, marine ostracod crustacean luciferin causes chemiluminescence by reacting with albumin in culture media, although a quantum yield is low. Since the self-luminescence does not depend on the amount of luciferase, it is observed as the background in an intracellular imaging of marine ostracod crustacean luciferase and the measurement of the transcription activity. It has been desired to develop marine ostracod crustacean luciferin analogs having the low background.

A marine ostracod crustacean luciferin derivative has been synthesized and a chemiluminescence reagent used for the quantification of super oxide anion has been invented. However, no derivative which becomes the substrate of marine ostracod crustacean luciferase has been developed.

Patent Document 1: WO90/01542
Patent Document 2: JP 1991-30678-A
Patent Document 3: JP 2004-187652-A
Patent Document 4: JP 2005-169768-A
Patent Document 5: PCT/JP03/15828
Patent Document 6: JP 1993-60697-A Publication
Patent Document 7: JP 1993-286976-A Publication
Non-patent Literature 1: Thompson, E. M., Nagata, S. & Tsuji, F. I. Vargula hilgendorfii luciferase: a secreted reporter enzyme for monitoring gene expression in mammalian cells. Gene 96, 257-62 (1990)
Non-patent Literature 2: Nakajima Y, Kobayashi K, Yamagishi K, Enomoto T and Ohmiya Y: cDNA cloning and characterization of a secreted luciferase from the luminous Japanese ostracod, Cypridina noctiluca. Biosci. Biotechnol. Biochem. 68, 565-70, 2004
Non-patent Literature 3: Inouye, S., Ohmiya, Y., Toya, Y. & Tsuji, F. Imaging of luciferase secretion from transformed Chinese hamster ovary cells. Proc. Natl. Acad. Sci. USA 89, 9584-7 (1992)
Non-patent Literature 4: Tanahashi, Y., Ohmiya, Y., Honma, S., Katsuno, Y., Ohta, H., Nakamura, H., Honma, K. Continuous measurement of targeted promoter activity by a secreted bioluminescence reporter, Vargula hilgendorfii luciferase. Anal Biochem. 289, 260-6 (2001)
Non-patent Literature 5: Kishi, Y.; Goto, T.; Inoue, S.; Sugiura, S.; Kishimoto, H. Tetrahedron Lett. 1966, 3445-3450
Non-patent Literature 6: Karpetsky, T. P.; White, E. H. J. Am. Chem. Soc. 1971, 93, 2333-2334
Non-patent Literature 7: Nakamura, H. Aizawa, M. Takeuchi, D. Murai, A. Shimomura O. Tetrahedron Lett. 2000, 41, 2185

BRIEF SUMMARY OF THE INVENTION

Not Applicable

DETAILED DESCRIPTION OF THE INVENTION

Figure 1:
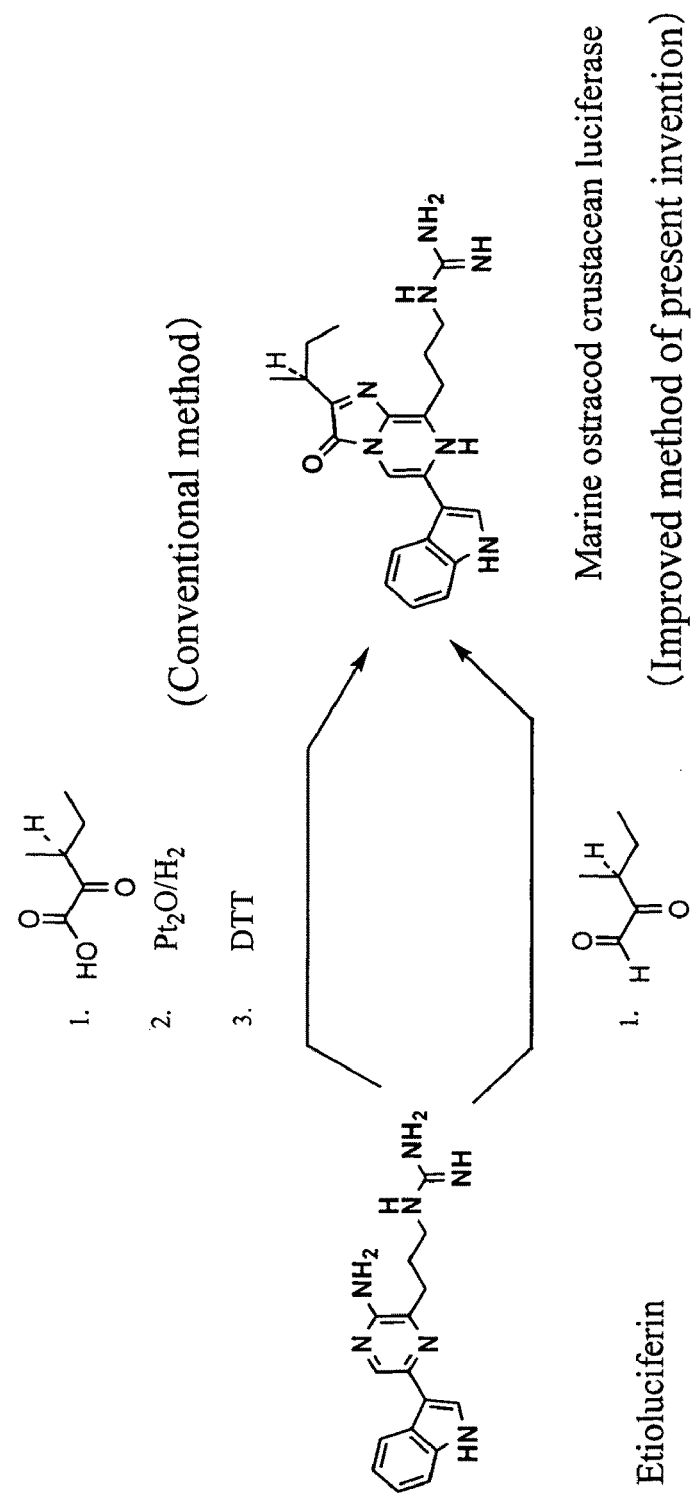
FIG. 1 is a view showing the comparison between the conventional synthesis and the synthesis of the present invention for native luciferin of marine ostracod crustacean.

Problem to be Solved by the Invention

It is an object of the present invention to solve the problems of many steps and low yields in a conventional method for producing optically active luciferin and to establish luciferin having the different luminescence wavelength and supply of luciferin.

Means for Solving the Problem

The present invention provides the following novel luciferin (luminescent substrate) which reacts with marine ostracod crustacean luciferase and a method for production thereof.

[1] A method for producing a compound represented by a general formula (2) characterized in that a compound represented by a general formula (1) is reacted with a diazomethane compound followed by being reacted with oxidants and at least one selected from the group consisting of alcohols and glycols:

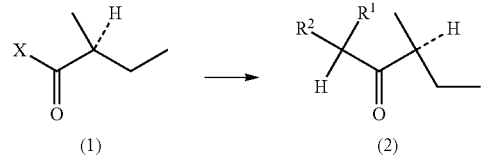

wherein, X represents Cl or Br;
$R^1$ and $R^2$ are the same or different, represent lower alkoxy groups, or aralkyloxy groups which may be substituted, or $R^1$ and $R^2$ are taken together with carbon atoms to which they are bound to represent a carbonyl group, or $R^1$ and $R^2$ are taken together to represent an alkylenedioxy group.

[2] A compound represented by a general formula (2):

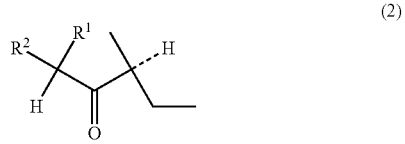

wherein $R^1$ and $R^2$ are the same or different, represent lower alkoxy groups, or aralkyloxy groups which may be substituted, or R¹ and R² are taken together with carbon atoms to which they are bound to represent a carbonyl group, or R¹ and R² are taken together to represent an alkylenedioxy group.

[3] A method for producing marine ostracod crustacean luciferin represented by a general formula (4) or a derivative thereof characterized in that a compound represented by a general formula (2) is reacted with a compound represented by a general formula (3):

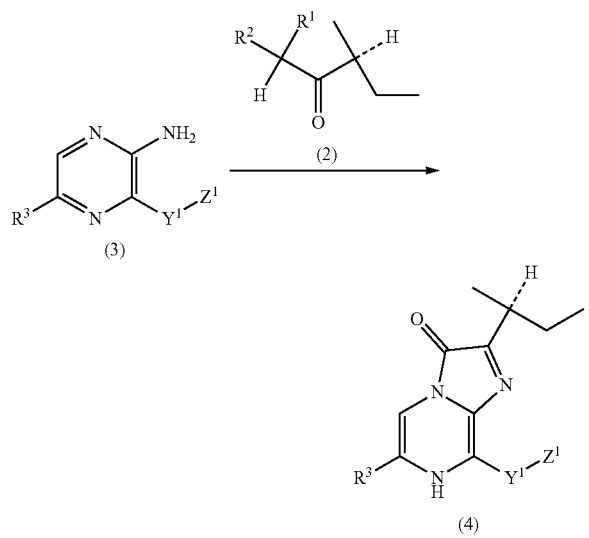

wherein R¹ and R² are the same or different, represent lower alkoxy groups, or aralkyloxy groups which may be substituted, or R¹ and R² are taken together with carbon atoms to which they are bound to represent a carbonyl group, or R¹ and R² are taken together to represent an alkylenedioxy group;

R³ represents an aryl group which may be substituted or a heterocyclic group which may be substituted;

Y¹ represents a lower alkylene group or a lower alkenylene group which may be substituted; and Z¹ represents an amino group, mono-lower alkylamino group, di-lower alkylamino group, guanidino group, amidino group, or an amino group, guanidino group or amidino group protected with a protecting group.

[4] A method for producing a marine ostracod crustacean luciferin analog represented by a general formula (7) characterized in that a compound represented by a general formula (5) is reacted with a compound represented by a general formula (6):

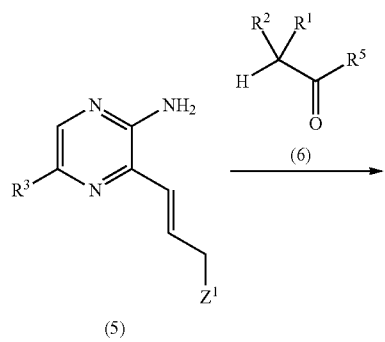

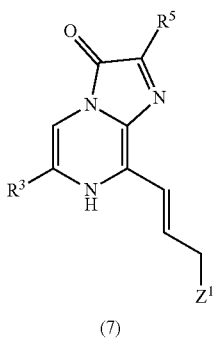

wherein R¹ and R² are the same or different, represent lower alkoxy groups, or aralkyloxy groups which may be substituted, or R¹ and R² are taken together with carbon atoms to which they are bound to represent a carbonyl group, or R¹ and R² are taken together to represent an alkylenedioxy group;

R³ represents an aryl group which may be substituted or a heterocyclic group which may be substituted;

R⁵ represents a lower alkyl group which may be substituted with fluorine atoms, a cycloalkyl group which may be substituted with fluorine atoms, a 5- or 6-membered aromatic group or heterocyclic group, or an aralkyl group; and Z¹ represents an amino group, mono-lower alkylamino group, di-lower alkylamino group, guanidino group, amidino group, or an amino group, guanidino group or amidino group protected with a protecting group.

[5] A compound represented by a general formula (7):

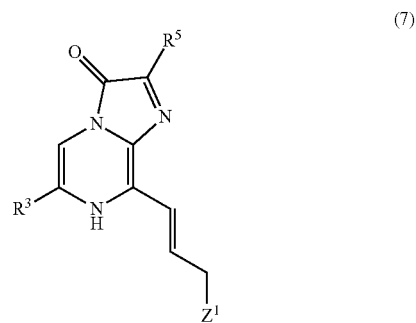

wherein R³ represents an aryl group which may be substituted or a heterocyclic group which may be substituted;

R⁵ represents a lower alkyl group which may be substituted with fluorine atoms, a cycloalkyl group which may be substituted with fluorine atoms, a 5- or 6-membered aromatic group or heterocyclic group, or an aralkyl group; and Z¹ represents an amino group, mono-lower alkylamino group, di-lower alkylamino group, guanidino group, amidino group, or an amino group, guanidino group or amidino group protected with a protecting group.

[6] A method for producing a marine ostracod crustacean luciferin derivative represented by a general formula (8) characterized in that a compound represented by a general formula (3) is reacted with a compound represented by a general formula (6):

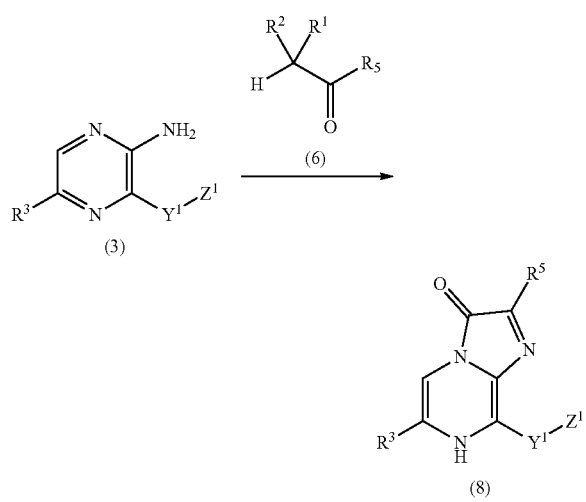

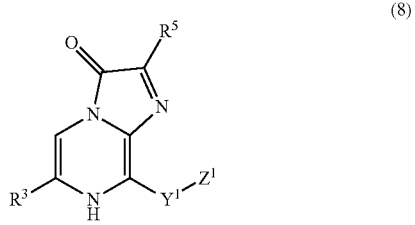

wherein $R^1$ and $R^2$ are the same or different, represent lower alkoxy groups, or aralkyloxy groups which may be substituted, or $R^1$ and $R^2$ are taken together with carbon atoms to which they are bound to represent a carbonyl group, or $R^1$ and $R^2$ are taken together to represent an alkylenedioxy group;
$R^3$ represents an aryl group which may be substituted or a heterocyclic group which may be substituted;
$R^5$ represents a lower alkyl group which may be substituted with fluorine atoms, a cycloalkyl group which may be substituted with fluorine atoms, a 5- or 6-membered aromatic group or heterocyclic group, or an aralkyl group;
$Y^1$ represents a lower alkylene group or a lower alkenylene group which may be substituted; and
$Z^1$ represents an amino group, mono-lower alkylamino group, di-lower alkylamino group, guanidino group or amidino group, or an amino group, guanidino group or amidino group protected with a protecting group.

[7] A compound represented by a general formula (8) or a salt thereof:

(8)

wherein $R^3$ represents an aryl group which may be substituted or a heterocyclic group which may be substituted;
$R^5$ represents a lower alkyl group which may be substituted with fluorine atoms, a cycloalkyl group which may be substituted with fluorine atoms, a 5- or 6-membered aromatic group or heterocyclic group, or an aralkyl group;
$Y^1$ represents a lower alkylene group or a lower alkenylene group which may be substituted; and
$Z^1$ represents an amino group, mono-lower alkylamino group, di-lower alkylamino group, guanidino group, amidino group, or an amino group, guanidino group or amidino group protected with a protecting group;
but when $R^3$ is indolyl or phenyl, $Y^1$ is propylene and $Z^1$ is guanidino, $R^5$ is not sec-butyl.

[8] The compound or the salt thereof according to [5] or [7] having a lower background than native luciferin of marine ostracod crustacean.

[9] The compound according to [5] or [7] or the salt thereof characterized in that a maximum luminescence wavelength when reacted with marine ostracod crustacean luciferase is different from that of native luciferin of marine ostracod crustacean.

[10] A compound represented by the following formula or a salt thereof.

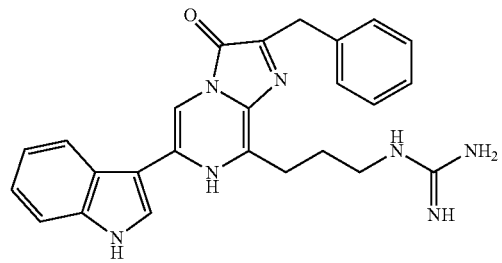 [SMILES: N=C(N)NCCCc1[nH]c(-c2c[nH]c3ccccc23)cn2c(=O)c(Cc3ccccc3)nc1-2]

[11] A compound represented by the following formula or a salt thereof.

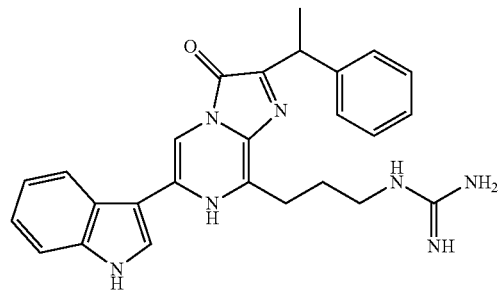 [SMILES: CC(c1ccccc1)c1nc2c(CCCNC(=N)N)[nH]c(-c3c[nH]c4ccccc34)cn-2c1=O]

[12] A compound represented by the following formula or a salt thereof.

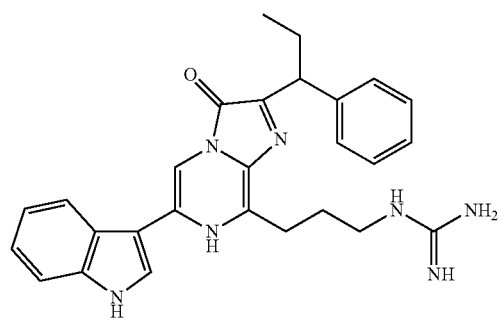 [SMILES: CCC(c1ccccc1)c1nc2c(CCCNC(=N)N)[nH]c(-c3c[nH]c4ccccc34)cn-2c1=O]

[13] A compound represented by the following formula or a salt thereof.

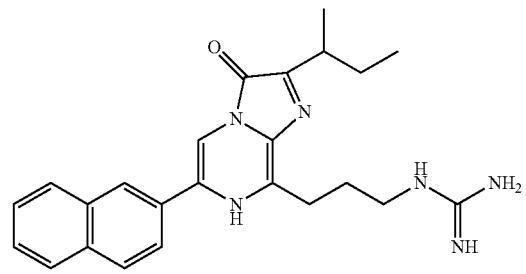 [SMILES: CCC(C)c1nc2c(CCCNC(=N)N)[nH]c(-c3ccc4ccccc4c3)cn-2c1=O]

[14] A compound represented by the following formula or a salt thereof.

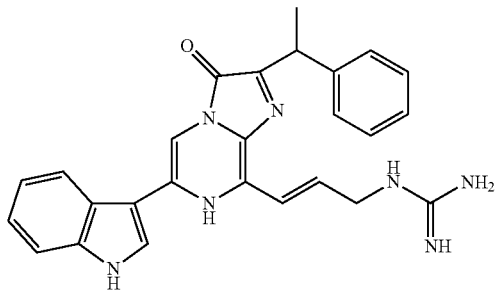 [SMILES: CC(c1ccccc1)c1nc2c(/C=C/CNC(=N)N)[nH]c(-c3c[nH]c4ccccc34)cn-2c1=O]

[15] A marine ostracod crustacean luciferin stabilization composition comprising marine ostracod crustacean luciferin or an analog thereof and an antioxidant.

[16] A method for storing marine ostracod crustacean luciferin or an analog thereof characterized by storing marine ostracod crustacean luciferin or the analog thereof in the presence of an antioxidant.

[17] A kit for using in a marine ostracod crustacean biological luminescence system, comprising marine ostracod crustacean luciferin or an analog thereof and an antioxidant.

[18] Use of at least one antioxidant for reducing a background in a marine ostracod crustacean biological luminescence system.

[19] A method for measuring biological luminescence in a marine ostracod crustacean system characterized in that the biological luminescence is measured in the presence of an antioxidant in a biological luminescence measurement system of marine ostracod crustacean luciferase and marine ostracod crustacean luciferin or an analog thereof.

[20] The method, the composition or the kit according to [15] to [20] wherein the antioxidant is selected from the group consisting of ascorbic acid or salts thereof, erythorbic acid or salts thereof, dithionous acid or salts thereof, hydrogen sulfite salts, sulfite salts, pyrosulfite salts, metabisulfite salts, cysteine, thioglycerol, butylhydroxyanisole, polyphenols, thiosulfuric acid or salts thereof and borohydride alkali metals.

EFFECT OF THE INVENTION

According to the present invention, optically active marine ostracod crustacean luciferin is now able to be produced by the simple method. This is because an objective optically active compound of the general formula (4) can be obtained with high yield in one step reaction by condensing the compound of the general formula (2) and the compound of the general formula (3) (FIG. 1).

The compounds of the general formulae (7) and (8) of the present invention were able to shift the luminescence wavelength generated by marine ostracod crustacean luciferase.

For example, in the compound 36 of the present invention, the maximum luminescence wavelength is shifted to 390 nm, and this compound can emit the light in an ultraviolet region. By making analogs of the compound 36, it is possible to easily synthesize the analog having the maximum luminescence wavelength of about 380 to 400 nm. The light in such a wavelength range is absorbed by various compounds, and can activate various chemicals (e.g., anticancer agents and rhodopsin).

When the marine ostracod crustacean system biological luminescence using luciferin or the derivative thereof is measured in the presence of the antioxidant, particularly ascorbic acid or the salt thereof or erythorbic acid or the salt thereof, the background is reduced and an S/N ratio is improved.

In an expression system containing marine ostracod crustacean luciferase (enzyme) or a marine ostracod crustacean luciferase gene in the cell, albumin such as BSA is often combined to stabilize luciferase. The antioxidant such as ascorbic acid and sulfite salts (e.g., $Na_2SO_3$) can inhibit the increase of the background caused by albumin.

BEST MODES FOR CARRYING OUT THE INVENTION

The alkylenedioxy group herein include alkylenedioxy groups having 2 to 6 carbon atoms, preferably 2 to 4 carbon atoms, e.g., ethylenedioxy, propylenedioxy, butylenedioxy, pentylenedioxy and hexylenedioxy.

The diazomethane compound includes diazomethane and trimethylsilyl diazomethane.

The lower alkyl group includes straight or branched alkyl groups having 1 to 6 carbon atoms, particularly 1 to 4 carbon atoms, e.g., methyl, ethyl, n-propyl, isopropyl, n-butyl, isobutyl, sec-butyl (in the case of $R^5$, optically active sec-butyl is preferable), t-butyl, pentyl and hexyl.

The lower alkyl group substituted with fluorine atoms includes fluoro lower alkyl groups composed of fluorine, hydrogen and carbon atoms, and perfluoro lower alkyl groups composed of fluorine and carbon atoms. The fluoro lower alkyl group includes lower alkyl groups obtained by substituting one or more (not all) hydrogen atoms in the above lower alkyl group with the fluorine atoms. The perfluoro lower alkyl group includes lower alkyl groups obtained by substituting all hydrogen atoms in the above lower alkyl group with the fluorine atoms. The perfluoro lower alkyl group represented by $R^5$ includes straight or branched perfluoroalkyl groups having 1 to 6 carbon atoms, e.g., $CF_3$, $CF_2CF_3$, $CF_2CF_2CF_3$, $CF(CF_3)_2$, $CF_2CF_2CF_2CF_3$, $CF_2CF(CF_3)_2$, $CF(CF_3)CF_2CF_3$, $C(CF_3)_3$, $CF_2CF_2CF_2CF_2CF_2$, $CF_2CF(CF_3)CF_2CF_3$, $CF(CF_2CF_3)_2$, $C(CF_3)_2CF_2CF_3$, $CF_3CF_2CF_2CF_2CF_2CF_3$, $CF_2CF(CF_3)CF_2CF_2CF_3$, $CF(CF_2CF_3)(CF_2CF_2CF_3)$, $C(CF_3)_2CF_2CF_2CF_3$ and $C(CF_3)(CF_2CF_3)_2$, and preferably the branched perfluoroalkyl groups having 3 to 6 carbon atoms.

The fluoroalkyl group includes straight or branched fluoroalkyl groups having 1 to 6 carbon atoms obtained by substituting one or more (not all) hydrogen atoms in the above perfluoro lower alkyl group with the fluorine atoms, and preferably the branched fluoroalkyl group having 3 to 6 carbon atoms.

The cycloalkyl group includes cycloalkyl groups having 3 to 8 carbon atoms, preferably 5 to 6 carbon atoms, e.g., cyclopropyl, cyclobutyl, cyclopentyl, cyclohexyl, cycloheptyl and cyclooctyl.

The cycloalkyl group substituted with the fluorine atoms includes fluorocycloalkyl groups composed of fluorine, hydrogen and carbon atoms, and perfluorocycloalkyl groups composed of fluorine and carbon atoms. The fluorocycloalkyl group includes cycloalkyl groups obtained by substituting one or more (not all) hydrogen atoms in the above cycloalkyl group with the fluorine atoms. The perfluorocycloalkyl group includes cycloalkyl groups obtained by substituting all hydrogen atoms in the above cycloalkyl group with the fluorine atoms.

The 5- or 6-membered aromatic ring or heterocyclic group represented by $R^5$ includes phenyl, pyridyl, pyrrolyl, imidazolyl, thiazolyl, isothiazolyl, oxazolyl, isoxazolyl, pyrimidinyl, pyrazinyl, thienyl, furyl and pyridazinyl.

The lower alkoxy group includes straight or branched alkoxy groups having 1 to 6 carbon atoms, preferably 1 to 4 carbon atoms, e.g., methoxy, ethoxy, n-propoxy, isopropoxy, n-butoxy, isobutoxy, sec-butoxy, t-butoxy, pentoxy and hexyloxy.

The mono lower alkylamino group includes amino groups mono-substituted with the straight or branched alkyl group having 1 to 6 carbon atoms, preferably 1 to 4 carbon atoms, e.g., methylamino, ethylamino, n-propylamino, isopropylamino, n-butylamino, isobutylamino, sec-butylamino, tert-butylamino, pentylamino and hexylamino.

The di-lower alkylamino group includes amino groups di-substituted with the straight or branched alkyl group having 1 to 6 carbon atoms, preferably 1 to 4 carbon atoms, e.g., dimethylamino, diethylamino, di-n-propylamino, diisopropylamino, di-n-butylamino, diisobutylamino, di-sec-butylamino, di-tert-butylamino, dipentylamino and dihexylamino.

The heterocyclic group represented by $R^3$ includes heterocyclic groups obtained by condensing one 6-membered aromatic ring (may be a hetero ring) and one 5- or 6-membered ring, e.g., 3-indolyl, 1-isoindolyl, 3H-indol-2-yl, 1H-indazol-3-yl, 3-isoquinolynyl, 1-isoquinolynyl, (2-, 3- or 4-) quinolynyl, 1-phthalazinyl, 2-naphthylidyl, 2-quinazolyl, 2-benzimidazolyl, (2- or 3-)benzofuran, 1-isobenzofuran, (2- or 3-)benzothiophene and 1-isobenzothiophene.

Substituents for the heterocyclic group, aralkyl group, aralkyloxy group and aryl group include halogen atoms (particularly chlorine and fluorine atoms), methyl, ethyl, acetyl, methoxy, OH, SH, COOH, amino, methylamino, dimethylamino, nitro, cyano, and trifluoromethyl, and they may be substituted with 1 to 3 of these substituents.

The aryl group represented by $R^3$ includes naphthyl, phenyl, biphenyl, anthranil, phenanthreyl, fluorenyl, indenyl, phenalenyl, acenaphthylenyl and pyrenyl.

The aralkyl groups includes aralkyl groups having 7 to 12 carbon atoms, e.g., benzyl, 1-phenethyl, 2-phenethyl, 1-phenylpropyl, 2-phenylpropyl, 3-phenylpropyl and naphthylmethyl.

The aralkyloxy group includes aralkyloxy groups having 7 to 12 carbon atoms, e.g., benzyloxy, 1-phenethyloxy, 2-phenethyloxy, 1-phenylpropyloxy, 2-phenylpropyloxy, 3-phenylpropyloxy and naphthylmethyloxy.

As the protecting group of the amino, guanidino or amidino group represented by $Z^1$, standard protecting groups such as tert-butoxycarbonyl (BOC), benzyloxycarbonyl (Cbz) and Fmoc can be widely exemplified.

The lower alkylene group represented by $Y^1$ includes alkylene groups having 1 to 6 carbon atoms, preferably 1 to 4 carbon atoms, e.g., $CH_2$, $CH(CH_3)$, $CH_2CH_2$, $CH_2CH(CH_3)$, $CH(CH_3)CH_2$, $CH_2CH_2CH_2$, $CH_2CH(CH_3)CH_2$, $CH_2CH_2CH_2CH_2$, and the lower alkenylene group represented by $Y^1$ includes alkenylene groups having 1 to 6 carbon atoms, preferably 1 to 4 carbon atoms, e.g., $CH=CH$, $CH=C(CH_3)$, $C(CH_3)=CH$, $CH=CHCH_2$, $CH=C(CH_3)CH_2$, $CH_2CH=CH$, $CH=CHCH_2CH_2$.

Subsequently, the method for producing the compound 2 shown in Scheme 1 will be described.

<Scheme 1>

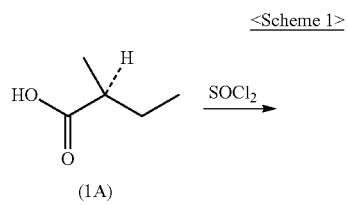

(1A)

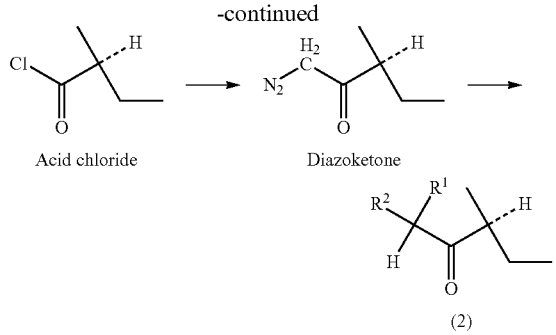

(2)

In the formula, $R^1$ and $R^2$ are the same as defined above.

This method is composed three steps using Arndt-Eistert reaction as a key reaction. First, acid chloride is obtained by using thionyl chloride at about 1 M up to in an excessive amount for 1 M of (+)-2-methylbutyric acid (1A) and reacting them at room temperature for 1 to 24 hours. Subsequently, resulting acid chloride is reacted with 2 equivalents of trimethylsilyl diazomethane or diazomethane at 0 to 4° C. for 1 to 4 hours to yield a diazoketone compound. A novel optically active compound (2) can be yielded by reacting the resulting diazoketone compound with an oxidant (particularly, tert-butyl hypochloride) at about one equivalent in the presence of alcohol or glycol in an equivalent or excessive amount at 0 to 4° C. for 1 to 2 hours. When $R^1$ and $R^2$ are benzyloxy groups, a compound (aldehyde body) of the general formula (2) can be yielded by hydrogenolysis in the presence of platinum oxide in a catalytic amount.

The oxidant includes tert-butyl hypochloride.

$R^1$ and $R^2$ are introduced according to alcohol (straight or branched lower alcohol having 1 to 6 carbon atom, e.g., methanol, ethanol, n-propanol, isopropanol, n-butanol, isobutanol, sec-butanol and tert-butanol; or aralkyl alcohol such as benzyl alcohol which may have the substituent) or glycol (glycol having 2 to 6 carbon atoms, e.g., ethylene glycol, 1,2-propylene glycol, 1,3-propylene glycol, 1,2-butylene glycol, 1,3-butylene glycol, 1,3-butylene glycol, 1,4-butylene glycol and 2,3-butylene glycol) combined with the oxidant. For example, when methanol is used, both $R^1$ and $R^2$ are methoxy groups, and when benzyl alcohol is used, both $R^1$ and $R^2$ are benzyloxy groups. When methanol and ethanol are combined, the compound in which $R^1$ and $R^2$ are methoxy and ethoxy is obtained.

In one embodiment of the present invention, the aralkyloxy group having the substituent includes aralkyloxy groups substituted with 1 to 3 substituents such as hydroxy, lower alkoxy, cyano, nitro, amino, mono lower alkylamino, di lower alkylamino, halogen atoms (F, Cl, Br, I), lower alkyl, SH, alkylthio (S-lower alkyl) and ethylenedioxy.

<Scheme 2>

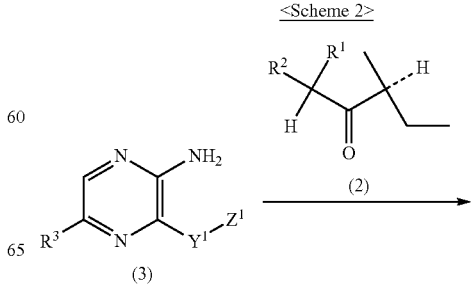

(3) → (2)

-continued

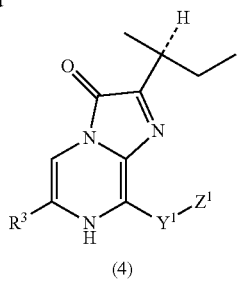

(4)

In the formulae, $R^1$, $R^2$, $R^3$, $Y^1$ and $Z^1$ are the same as defined above.

The reaction is promoted advantageously by using about 1 to 4 M of the compound of the general formula (2) for 1 M of the compound of the general formula (3) and reacting them in the presence or absence of an acid at about 65 to 100° C. for 1 to 2 hours.

The method for producing the compound of the general formula (3) will be described in Scheme 3.

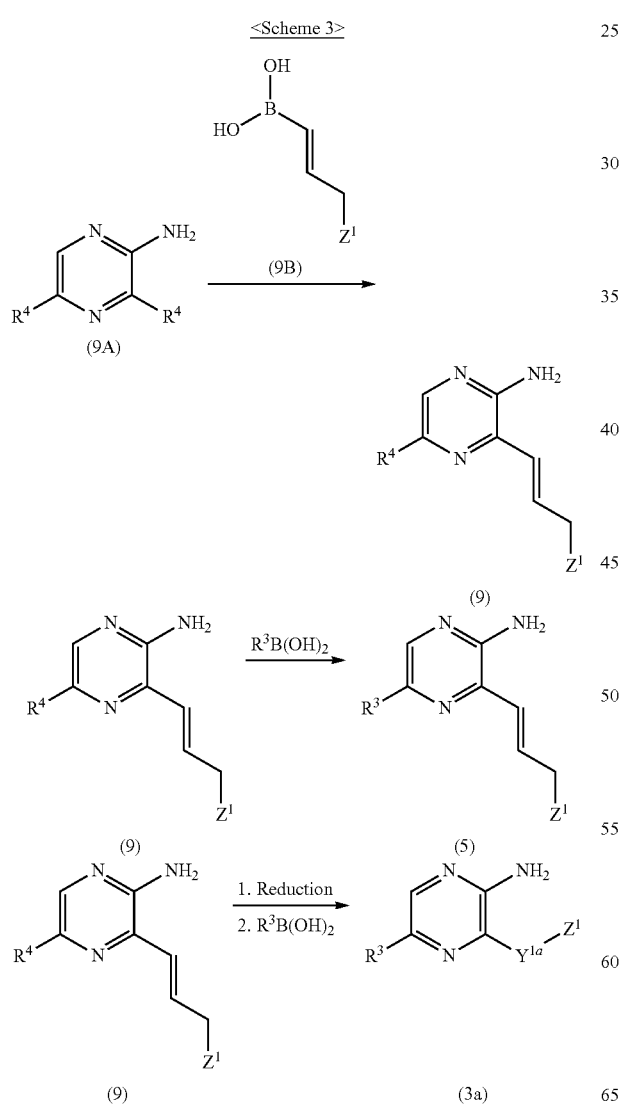

In the formulae, $R^3$ and $Z^1$ are the same as defined above; $Y^{1a}$ represents $CH_2CH_2CH_2$; and $R^4$ represents a halogen atom, particularly Br or Cl.

The method for producing the compound of the general formula (5) shown in Scheme 3 or the general formula (3) will be described.

$Z^1$ represents an amino group, mono-lower alkylamino group, di-lower alkylamino group, guanidino group or amidino group, or an amino group, guanidino group or amidino group protected with the protecting group. In the method for producing the above intermediate, $Z^1$ is preferably the amino group, guanidino group or amidino group protected with the protecting group.

The method for producing the compound of the general formula (5) or (3) uses Suzuki coupling reaction as the key reaction. A vinylboronic acid reagent (9B) at 1 M is used for 1 M of well-known 2-amino-3,5-di-halogenated aminopyrazine (9A), and they are reacted in the presence of palladium catalyst and a base for 1 to 2 hours to yield an olefin compound (general formula (9)). The compound of the general formula (5) can be yielded from the resulting compound of the general formula (9) by Suzuki coupling reaction using $R^3B(OH)_2$.

Meanwhile, the compound of the general formula (3a) can be yielded by reducing olefin with hydrogenation in the presence of 10% mol of platinum oxide relative to 1 M of the olefin compound (9) followed by Suzuki coupling reaction using $R^3B(OH)_2$.

The method for producing the compound of the general formula (7) will be described in the following Scheme 4.

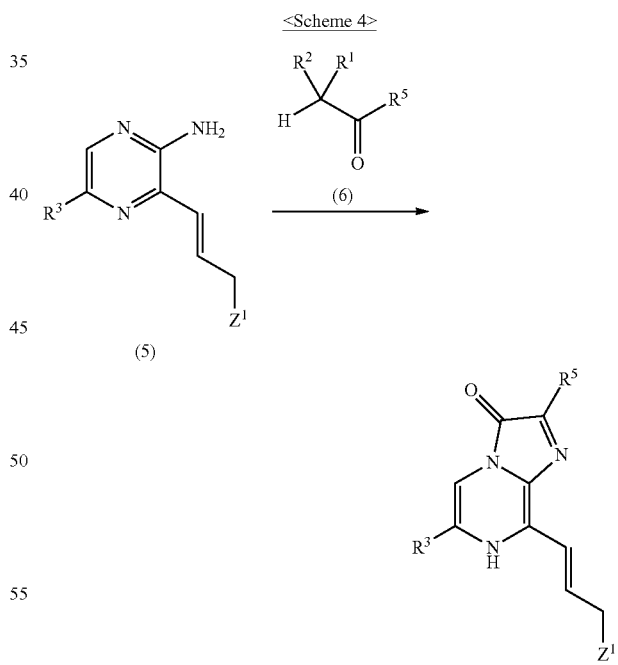

In the formulae, $R^1$, $R^2$, $R^3$, $R^5$ and $Z^1$ are the same as defined above.

The compound of the general formula (6) at about 1 to 4 M is used for 1 M of the compound of the general formula (5), and they are reacted in the presence or absence of the acid at a temperature of 65 to 100° C. for 1 to 2 hours to yield the compound of the general formula (7).

<Scheme 5>

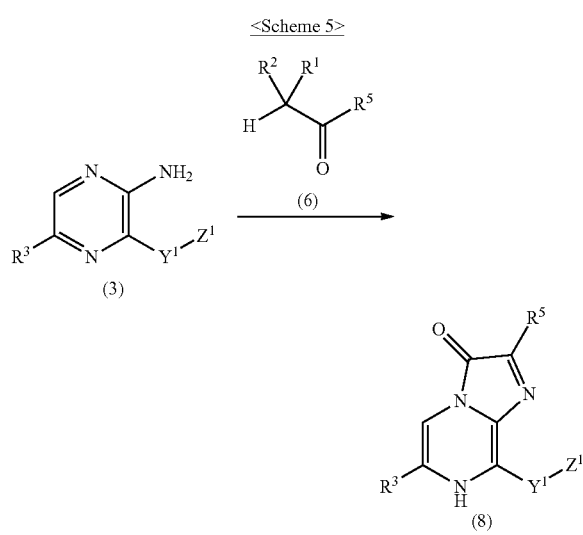

In the formulae, $R^1$, $R^2$, $R^3$, $R^5$, $Y^1$ and $Z^1$ are the same as defined above.

The compound of the general formula (6) at about 1 to 4 M is used for 1 M of the compound of the general formula (3), and they are reacted in the presence or absence of the acid at a temperature of 65 to 100° C. for 1 to 2 hours to yield the compound of the general formula (8).

The compound of the present invention is useful as marine ostracod crustacean luciferin.

In one preferable embodiment, when the compound of the present invention is reacted with marine ostracod crustacean luciferase, the maximum luminescence wavelength is shifted by 15 nm or more to a long or short wavelength side compared with that of native marine ostracod crustacean luciferin. Thus, the compound of the present invention can be measured distinctly from *Renilla* luciferin.

Furthermore, in one preferable embodiment, the compound of the present invention is the stable compound and has the low background. Specifically, the compound of the present invention has the background which is about 5% lower than that in native luciferin.

In the present invention, marine ostracod crustacean luciferin or the analog thereof can be stabilized by combining marine ostracod crustacean luciferin or the analog thereof with the antioxidant. Furthermore, by performing the measurement of the marine ostracod crustacean system biological luminescence containing marine ostracod crustacean luciferase and marine ostracod crustacean luciferin or the analog thereof in the presence of the antioxidant, it is possible to augment luminescence signals, lower the luminescence background and widely improve an S/N ratio.

The antioxidant includes ascorbic acid or salts thereof, erythorbic acid or salts thereof, dithionous acid or salts thereof, hydrogen sulfite salts, sulfite salts, pyrosulfite salts, metabisulfite salts, cysteine, thioglycerol, butylhydroxyanisole, polyphenols, thiosulfuric acid or salts thereof and borohydride alkali metals, and one or two or more thereof can be combined to use. Preferably, ascorbic acid, erythorbic acid and salts thereof are exemplified. When two or more antioxidants are combined, it is preferable to combine ascorbic acid with at least one other antioxidant.

Ascorbate, erythorbate, hydrogen sulfite, sulfite, pyrosulfite, metabisulfite and thiosulfate salts include alkali metal salts such as sodium, potassium, lithium and cesium salts, and alkali earth salts such as ammonium, calcium and magnesium salts. The borohydride alkali metal includes sodium borohydride ($NaBH_4$), potassium borohydride, lithium borohydride and cesium borohydride.

When ascorbic acid is added to the marine ostracod crustacean biological luminescence system, it is preferable to add at a concentration of about 0.05 to 1 M.

A composition comprising marine ostracod crustacean luciferin or the analog thereof and the antioxidant is suitable for stabilizing marine ostracod crustacean luciferin or the analog thereof (solution or solid such as powder, granule or crystal). In the composition, about 40,000 to 800,000 parts by weight of the antioxidant is used per one part by weight of marine ostracod crustacean luciferin or the analog thereof.

Marine ostracod crustacean luciferin or the analog thereof of the present invention is added to the system containing marine ostracod crustacean luciferin, and in such a system, a luciferase assay is often performed in the presence of about 0.1 to 1% of albumin (HAS or BSA, particularly BSA). The addition of albumin remarkably increases the background in the measurement system. However, when a reducing agent such as ascorbic acid or sodium sulfite is added to this measurement system, the increase of the background due to albumin can be remarkably inhibited.

Therefore, the composition comprising marine ostracod crustacean luciferin or the analog thereof and the antioxidant (particularly, ascorbic acid or sulfite salts) is particularly preferable because the composition not only can stabilize the storage of marine ostracod crustacean luciferin or the analog thereof at room temperature but also can inhibit the increase of the background upon measurement.

EXAMPLES

The present invention will be described below in more detail based on Examples.

Example 1

Production of Compound of General Formula (2A) (Optically Active 1,1-Diethoxy-3-methyl-pentan-2-one)

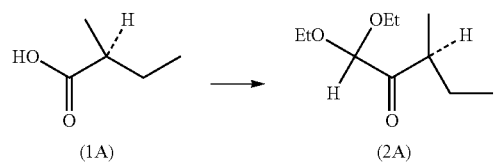

Thionyl chloride (1.2 mL) was instilled in a solution of optically active S-2-methylbutyric acid (1 g) in $CH_2Cl_2$ (10 mL). The mixture was stirred at room temperature for 24 hours. The reaction solution was concentrated to yield acid chloride. Acid chloride was dissolved in 1:1 THF-acetonitrile (15 mL), 2M $TMSCHN_2$ (10 mL) was added at 0° C., and after one hour, the solution was concentrated. The solution was dissolved in ethanol (10 mL), and tert-BuOCl (1 mL) was instilled thereto at 0° C. The reaction solution was stirred at 0° C. for one hour, concentrated and purified by a silica gel column (0.6 g, 39%). S-1,1-Diethoxy-3-methyl-pentan-2-one: $^1$H NMR (500 MHz, $CD_3Cl$) 0.86 (3H, t, J=7 Hz), 1.08 (3H, d, J=7 Hz), 1.24 (6H, t, J=7 Hz), 1.31-1.73 (2H, m), 2.93 (1H, q, J=7 Hz) 3.51-3.71 (4H, m), 4.63 (1H, s); IR (KBr) 2955, 2871, 1727, 1486, 1367, 1120, 1063 $cm^{-1}$, $[\alpha]_D^{24}$=+22 (c 1.0 dichloromethane).

Example 2

Production of Compound (Optically Active Marine Ostracod Crustacean Luciferin) of General Formula (11) Using Compounds of General Formula (2A) and General Formula (10)

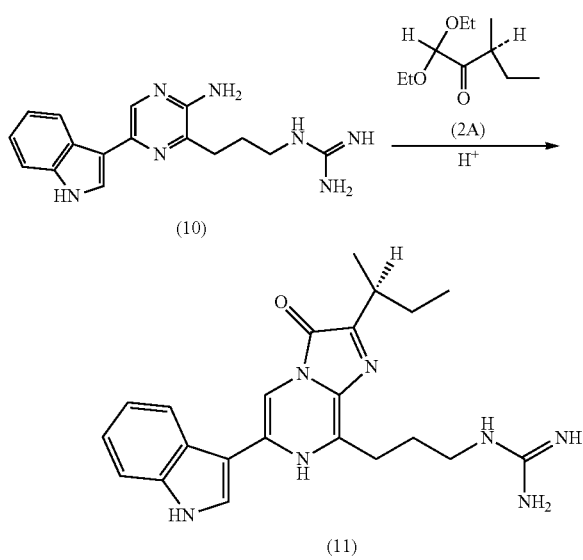

In a round bottom shaking flask (5 mL), the compound (10) (10 mg), water (0.1 mL), 1,1-Diethoxy-3-methyl-pentan-2-one (0.02 mL) and ethanol (0.1 mL) were heated at 80° C. for 30 minutes. Then, 48% HBr (0.02 mL) was added, the mixture was heated for additional 10 minutes, and then concentrated under reduced pressure. A residue was dissolved in ethanol, and purified using LH-20 column to yield the compound (11) (7.1 mg, 50%). $^1$H NMR (500 MHz, CD$_3$OD) 0.96 (3H, t, J=7 Hz), 1.45 (3H, d, J=7 Hz), 1.81-1.99 (2H, m), 2.33 (2H, quintet, J=7 Hz), 3.17 (1H, sextet, J=7 Hz), 3.41 (2H, q, J=7 Hz), 3.44 (2H, q, J=7 Hz), 7.18-7.21 (2H, m), 7.50 (1H, d, J=7 Hz), 8.01 (1H, s), 8.07 (1H, d, J=7 Hz), 8.44 (1H, s), $[a]_D^{24}$=+22 (0.046, Acetonitril-Water-10% TFA: 39-60-1). The resulting compound (11) exhibited an activity equivalent to that of native luciferin (Test Example 1).

Example 3

Production of Compound (Optically Active Marine Ostracod Crustacean Luciferin) of General Formula (11) Using Compounds of General Formula (12) and General Formula (10)

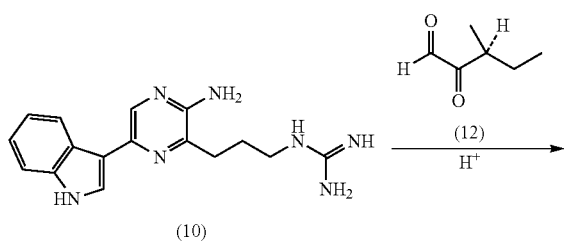

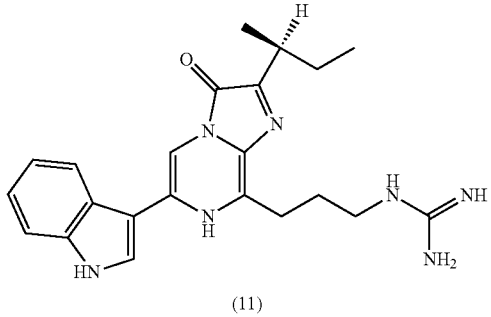

The compound (10) (11 mg), water (0.2 mL), (+)-sec-Butylglyoxal (0.01 mL) and methanol (0.1 mL) were added into a round bottom shaking flask (5 mL), and heated at 65° C. for one hour. The reaction solution was cooled to room temperature, then one drop of 48% HBr was added, and concentrated under reduced pressure. A residue was dissolved in ethanol, and purified using the LH-20 column to yield 4 mg of the compound (11) (31%). $^1$H NMR (500 MHz, CD$_3$OD) 0.96 (3H, t, J=7 Hz), 1.45 (3H, d, J=7 Hz), 1.81-1.99 (2H, m), 2.33 (2H, quintet, J=7 Hz), 3.17 (1H, sextet, J=7 Hz), 3.41 (2H, q, J=7 Hz), 3.44 (2H, q, J=7 Hz), 7.18-7.21 (2H, m), 7.50 (1H, d, J=7 Hz), 8.01 (1H, s), 8.07 (1H, d, J=7 Hz), 8.44 (1H, s).

Example 4

Production of Compounds of General Formulae (13) to (16)

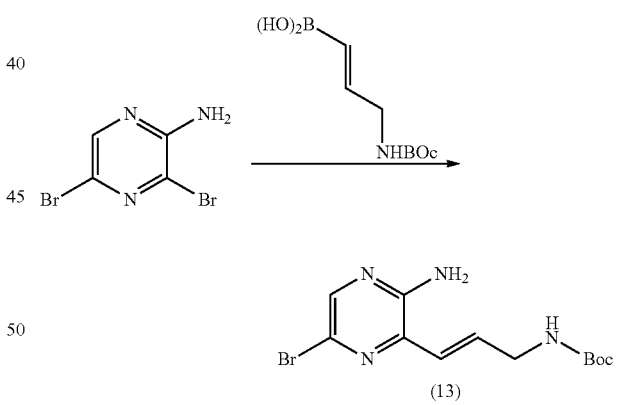

Synthesis of Compound (13)

Pd(PPh$_3$)$_4$ (50 mg) was added to a solution of 2-amino-3,5-dibromoaminopyrazine (1 g, 4 mM) and a vinylboronic acid reagent (0.8 g) in dioxane (72 mL)-saturated Na$_2$CO$_3$ (24 mL). The mixture was heated at 80° C. for one hour. After cooling, the reaction mixture was diluted with ethyl acetate, washed with brine and dried on sodium sulfate. A crude extract was yielded by filtrating followed by concentrating. The crude extract was purified by chromatography to yield a desired product (450 mg, 34%). $^1$H NMR (500 MHz, CDCl$_3$) 1.44 (9H, s), 3.96 (2H, br), 4.69 (2H, br), 4.82 (1H, br), 6.40 (1H, d, J=15 Hz), 6.87 (1H, br), 7.95 (1H, s).

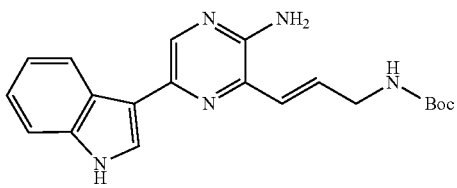

(14)

Synthesis of Compound (14)

Pd(PPh$_3$)$_4$ (30 mg) was added to a solution of the compound (13) (0.4 g, 1 mM) and 1-(phenylsulfonyl)3-indoleboronic acid (0.73 g, 2 mmol) in dioxane (50 mL)-saturated Na$_2$CO$_3$ (24 mL). The mixture was heated at 80° C. for one hour. After cooling, the reaction mixture was diluted with ethyl acetate, washed with brine and dried on sodium sulfate. A crude extract was yielded by filtrating followed by concentrating. The crude extract was purified by chromatography to yield a desired product. The desired product was dissolved in Methanol-Dioxane solution (8 mL), and 5 N sodium hydroxide (2 mL) was added, which was then stirred overnight. After working up, the mixture was purified by chromatography to yield the compound (14) (170 mg, 46%). $^1$H NMR (500 MHz, CDCl$_3$) 1.45 (9H, s), 4.04 (2H, br), 4.55 (2H, br), 4.80 (1H, br), 6.61 (1H, d, J=15 Hz), 6.94 (1H, br), 7.21-7.27 (2H, m), 7.41 (1H, d, J=7 Hz), 7.66 (1H, d, J=2.5 Hz) 8.41 (1H, br), 8.35 (1H, s).

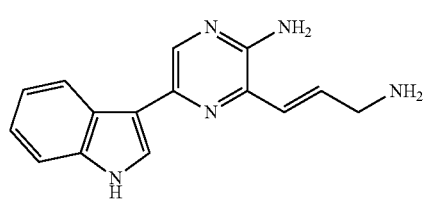

(15)

Synthesis of Compound (15)

The compound (14) was dissolved in a TFA (trifluoroacetic acid) solution, which was then stirred for one hour and concentrated. After the concentration, the resulting mixed solution was purified by chromatography to yield the compound (15) (170 mg). $^1$H NMR (500 MHz, CD$_3$OD) 3.85 (2H, d, J=7 Hz), 6.98-7.17 (4H, m), 7.41 (1H, d, J=7 Hz), 7.77 (1H, s), 8.28 (1H, d, J=7 Hz), 8.34 (1H, s).

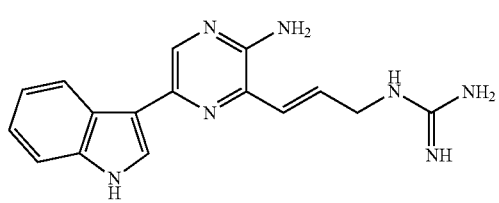

(16)

A solution of the compound (15) (150 mg, 0.6 mmol), Pyrazole-1-carboxamidine (175 mg) and DIEA (303 mg) in DMF was stirred at room temperature overnight. Ether was added to yield a precipitate. The precipitate was dissolved in methanol, and recrystallized to yield the compound (16) (95 mg, 53%). $^1$H NMR (500 MHz, CD$_3$OD) 4.20 (2H, d, J=7 Hz), 7.05-7.17 (4H, m), 7.43 (1H, d, J=7 Hz), 7.87 (1H, s), 8.12 (1H, d, J=7 Hz), 8.08 (1H, s).

Example 5

Production of Compound of General Formula (17) by Reacting Compound of General Formula (16) with Compound of General Formula (12)

Synthesis of Compound 17

In a round bottom shaking flask, the compound (16) (7 mg, 22 mmol), water (0.1 mL), the compound (12) (0.02 mL) and ethanol (0.05 mL) were heated at 100° C. for 30 minutes. Subsequently, 48% HBr (0.02 mL) was added, the mixture was heated for additional 10 minutes, and then concentrated under reduced pressure. A residue was dissolved in ethanol, and purified by the LH-20 column to yield the compound (17) (3.5 mg, 39%). $^1$H NMR (500 MHz, CD$_3$OD) 0.96 (3H, t, J=7 Hz), 1.44 (3H, d, J=7 Hz), 1.81-1.99 (2H, m), 4.20 (2H, d, J=7 Hz), 7.18-7.21 (4H, m), 7.42 (1H, d, J=7 Hz), 7.94 (1H, s), 8.07 (1H, d, J=7 Hz), 8.11 (1H, s).

Example 6

Synthesis of Compound of General Formula (10)

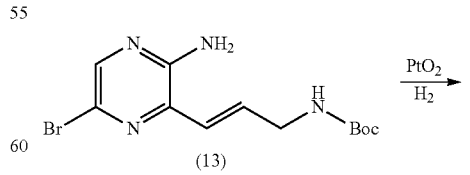

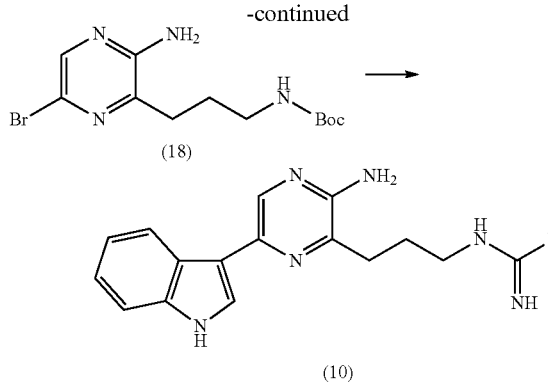

(18)

(10)

Synthesis of Compound (18)

The compound (13) (1 g, 0.3 mmol) was dissolved in ethanol (50 mL), and platinum oxide (100 mg) was added thereto. The mixture was vigorously agitated under a hydrogen atmosphere for 24 hours. The reaction solution was filtrated with aspiration using a glass filter with celite. A filtrate was concentrated, and purified by column chromatography to yield the compound (18) (800 mg, 79%). Physical property of the compound (18): $^1$H NMR (500 MHz, CDCl$_3$) 1.44 (9H, s), 2.03 (2H, d, J=7 Hz), 2.80 (2H, d, J=7 Hz), 3.28 (2H, d, J=7 Hz), 7.95 (1H, s).

The compound (10) was produced by the same method as the method for producing the compound (16) shown in Example 4. Physical property of the compound (10): $^1$H NMR (500 MHz, CDCl$_3$) 2.03 (2H, d, J=7 Hz), 2.80 (2H, d, J=7 Hz), 3.28 (2H, d, J=7 Hz), 7.08-7.16 (2H, m), 7.41 (1H, d, J=7 Hz) 7.90 (1H, s), 8.30 (1H, s).

Example 7

The compounds (24), (25), (26), (27) and (28) were synthesized by reacting the compound of the general formula (10) with the compounds (19), (20), (21), (22) and (23) comprised in the general formula (6).

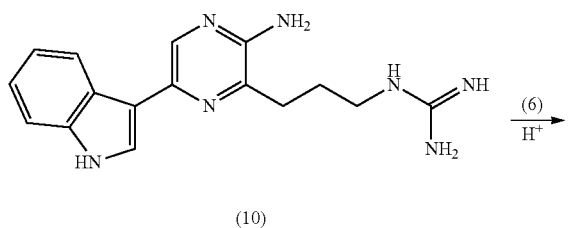

(10)

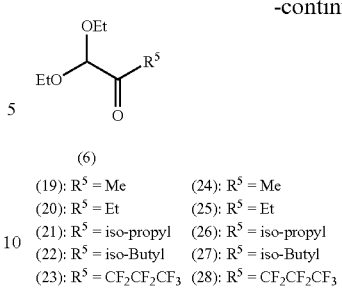

(6)

(19): R$^5$ = Me      (24): R$^5$ = Me
(20): R$^5$ = Et      (25): R$^5$ = Et
(21): R$^5$ = iso-propyl   (26): R$^5$ = iso-propyl
(22): R$^5$ = iso-Butyl    (27): R$^5$ = iso-Butyl
(23): R$^5$ = CF$_2$CF$_2$CF$_3$   (28): R$^5$ = CF$_2$CF$_2$CF$_3$

Synthesis of Compound (24)

In a round bottom shaking flask, the compound (10) (30 mg), water (0.4 mL), the compound (19) (0.030 mL), ethanol (0.2 mL) and 49% HBr (0.03 mL) were heated at 100° C. for one hour. The reaction solution was cooled to room temperature, and then concentrated under reduced pressure. A residue was dissolved in ethanol and purified by the LH-20 column to yield the compound (24) (15 mg, 38%). $^1$H-NMR (500 MHz, CD$_3$OD) 2.33 (2H, quintet, J=7 Hz), 2.54 (3H, s), 3.31 (2H, t, J=7 Hz), 3.43 (2H, t, J=7 Hz), 7.17-7.22 (2H, m), 7.47 (1H, d, J=7 Hz), 7.98 (1H, s), 8.01 (1H, d, J=7 Hz), 8.31 (1H, s); IR (KBr) 3376, 3175, 1661, 1550, 1454 cm$^{-1}$.

The compound (25) was obtained by the same method as the method for producing the compound (24). Physical property of the compound (25): $^1$H NMR (500 MHz, CD$_3$OD) 1.41 (3H, t, J=7 Hz), 2.33 (2H, quintet, J=7 Hz), 2.95 (2H, q, J=7 Hz), 3.35 (2H, t, J=7 Hz), 3.43 (2H, t, J=7 Hz), 7.16-7.22 (2H, m), 7.47 (1H, d, J=7 Hz), 7.99 (1H, s), 8.02 (1H, d, J=7 Hz), 8.35 (1H, s); IR (KBr) 3376, 3175, 1661, 1550, 1454 cm$^{-1}$.

The compound (26) was obtained by the same method as the method for producing the compound (24). Physical property of the compound (26): $^1$H NMR (500 MHz, CD$_3$OD) 1.50 (6H, t, J=7 Hz), 2.29 (2H, quintet, J=7 Hz), 3.32 (1H, sextet, J=7 Hz), 3.37 (2H, q, J=7 Hz), 3.43 (2H, q, J=7 Hz), 7.11-7.14 (2H, m), 7.40 (1H, d, J=7 Hz), 7.96 (1H, s), 7.94 (1H, d, J=7 Hz), 8.22 (1H, s); IR (KBr) 3376, 3175, 1655, 1548, 1452 cm$^{-1}$.

The compound (27) was obtained by the same method as the method for producing the compound (24). Physical property of the compound (27): $^1$H NMR (500 MHz, CD$_3$OD) 1.03 (6H, d, J=7 Hz), 2.18 (1H, m), 2.33 (2H, quintet, J=7 Hz), 2.78 (2H, d, J=7 Hz), 3.35 (2H, t, J=7 Hz), 3.43 (2H, t, J=7 Hz), 7.16-7.22 (2H, m), 7.47 (1H, d, J=7 Hz), 7.99 (1H, s), 8.04 (1H, d, J=7 Hz), 8.36 (1H, s); IR (KBr) 3376, 3175, 1661, 1550, 1454 cm$^{-1}$.

The compound (28) was obtained by the same method as the method for producing the compound (24). Physical property of the compound (28): $^1$H NMR (500 MHz, CD$_3$OD) 2.27 (2H, quintet, J=7 Hz), 2.99 (2H, t, J=7 Hz), 3.41 (2H, t, J=7 Hz), 7.14-7.22 (2H, m), 7.43 (1H, d, J=7 Hz), 7.87 (1H, s), 8.02 (1H, s), 8.06 (1H, d, J=7 Hz).

Example 8

Synthesis of Compound (30)

In a round bottom shaking flask, the compound (10) (10 mg), water (0.1 ml), the compound (29) (0.020 ml), ethanol (0.1 ml) and 49% HBr (0.01 mL) were heated at 100° C. for one hour. The reaction solution was cooled to room temperature, and then concentrated under reduced pressure. A residue was dissolved in ethanol and purified by the LH-20 column to yield the compound (30) (6 mg, 42%). $^1$H NMR (500 MHz, CD$_3$OD) 2.24 (2H, quintet, J=7 Hz), 3.25 (2H, t, J=7 Hz), 3.39 (2H, t, J=7 Hz), 4.27 (2H, s), 7.10 (2H, dd, J=7 Hz), 7.24 (1H, t, J=7 Hz), 7.30-7.45 (5H, m), 7.93 (1H, dd, J=7 Hz), 7.96 (1H, s), 8.27 (1H, s).

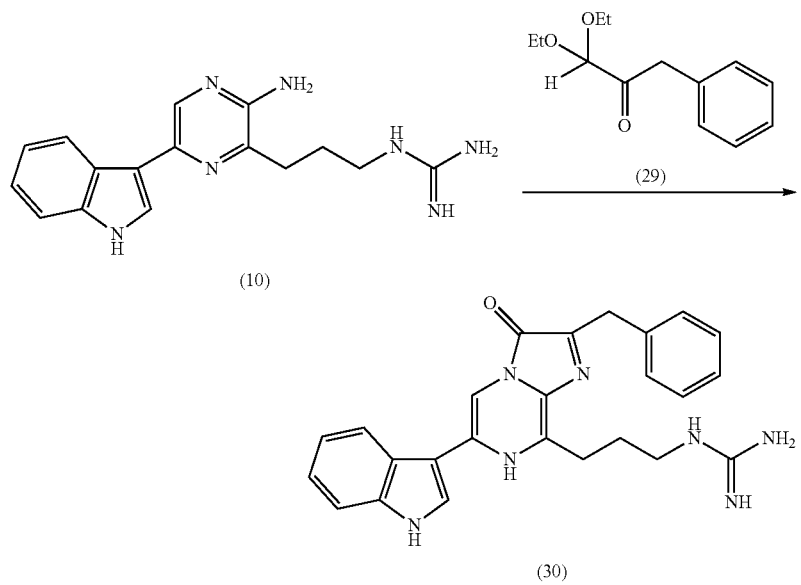

Synthesis of Compound (32)

In a round bottom shaking flask, the compound (10) (10 mg), water (0.1 ml), the compound (31) (0.020 ml), ethanol (0.1 ml) and 49% HBr (0.01 mL) were heated at 100° C. for one hour. The reaction solution was cooled to room temperature, and then concentrated under reduced pressure. A residue was dissolved in ethanol and purified by the LH-20 column to yield the compound (32) (5.0 mg, 34%). $^1$H NMR (500 MHz, CD$_3$OD) 1.84 (3H, d, J=7 Hz), 2.29 (2H, quintet, J=7 Hz), 3.38 (2H, t, J=7 Hz), 3.42 (2H, t, J=7 Hz), 4.60 (1H, q, J=7 Hz), 7.16 (2H, dd, J=7 Hz), 7.24 (1H, t, J=7 Hz), 7.32 (2H, t, J=7 Hz), 7.40 (2H, d, J=7 Hz), 7.43 (1H, dd, J=7 Hz) 7.97 (1H, dd, J=7 Hz), 7.98 (1H, s), 8.27 (1H, s).

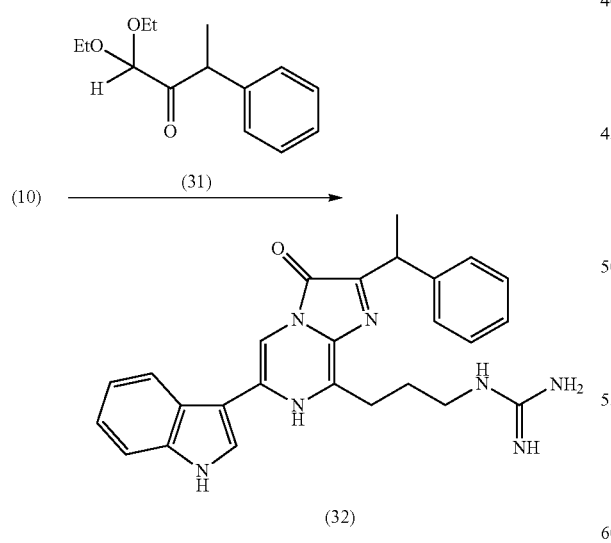

Synthesis of Compound (34)

In a round bottom shaking flask, the compound (10) (10 mg), water (0.1 ml), the compound (33) (0.020 ml), ethanol (0.1 ml) and 49% HBr (0.01 mL) were heated at 100° C. for one hour. The reaction solution was cooled to room temperature, and then concentrated under reduced pressure. A residue was dissolved in ethanol and purified by LH-20 column to yield the compound (34) (5.2 mg, 35%). $^1$H NMR (500 MHz, CD$_3$OD) 0.99 (3H, t, J=7 Hz) 1.84 (3H, d, J=7 Hz), 2.32 (4H, m), 3.41 (2H, t, J=7 Hz), 3.44 (2H, t, J=7 Hz), 4.29 (1H, t, J=7 Hz), 7.16-7.23 (3H, m), 7.30 (2H, t, J=7 Hz), 7.44 (2H, d, J=7 Hz), 7.47 (1H, dd, J=7 Hz) 7.95 (1H, dd, J=7 Hz), 7.97 (1H, s), 8.34 (1H, s).

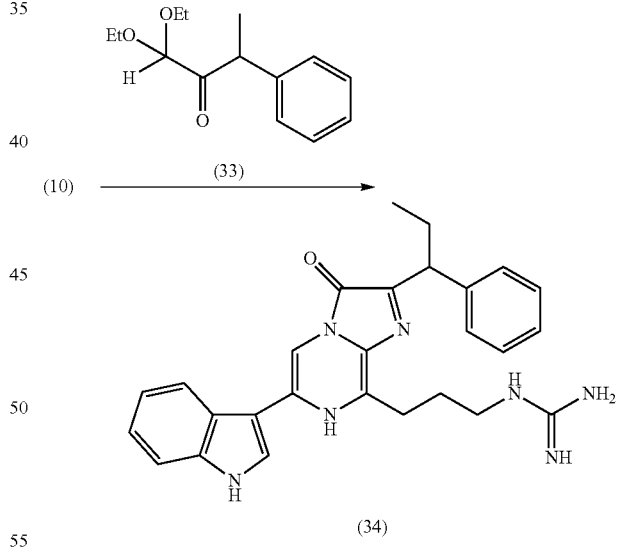

Synthesis of Compound (35)

Pd(PPh$_3$)$_4$ (40 mg) was added to a solution of the compound (13) (0.2 g, 0.6 mmol) and 2-naphthyl-boronic acid (103 mg, 0.6 mM) in dioxane (50 mL)-saturated Na$_2$CO$_3$ (24 mL). The mixture was heated at 80° C. for one hour. After cooling, the reaction mixture was diluted with ethyl acetate, washed with brine and dried on sodium sulfate. A crude extract was yielded by filtrating followed by concentrating. The crude extract was purified by chromatography to yield a desired product. The resulting compound was dissolved in 1 mL of TFA (trifluoroacetic acid), stirred for one hour, and concentrated. The trifluoroacetate compound was dissolved in 3.5 mL of DMF, and pyrasole-1-carboxamidine (280 mg) and DIEA (301 mg) were added thereto, and the mixture was stirred at room temperature overnight. Ether was added to yield a precipitate. The precipitate was dissolved in methanol, and recrystallized to yield the compound (35) (135 mg, 70%). $^1$H NMR (500 MHz, CD$_3$OD) 2.21 (2H, quintet, J=7 Hz), 2.90 (2H, t, J=7 Hz), 3.37 (2H, t, J=7 Hz), 7.46 (2H, d, J=7 Hz), 7.50 (1H, d, J=7 Hz), 7.86 (2H, d, J=7 Hz), 8.01 (1H, d, J=7 Hz), 8.30 (1H, s), 8.37 (1H, s).

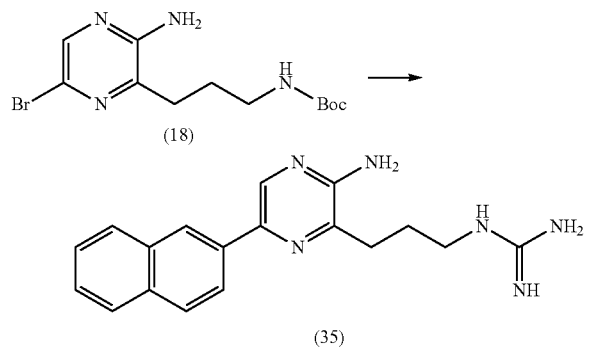

Synthesis of Compound (36)

In a round bottom shaking flask, the compound (35) (10 mg), water (0.1 ml), the compound (2A) (0.020 ml), ethanol (0.1 ml) and 49% HBr (0.01 mL) were heated at 100° C. for one hour. The reaction solution was cooled to room temperature, and then concentrated under reduced pressure. A residue was dissolved in ethanol and purified by the LH-20 column to yield the compound (36) (3.5 mg, 27%). $^1$H NMR (500 MHz, CD$_3$OD) 0.96 (3H, t, J=7 Hz), 1.47 (3H, d, J=7 Hz) 1.86 (2H, m), 2.35 (2H, quintet, J=7 Hz), 3.19 (1H, m), 3.43 (2H, t, J=7 Hz), 3.48 (2H, t, J=7 Hz), 7.55 (2H, d, J=7 Hz), 7.90 (1H, d, J=7 Hz), 8.01 (2H, d, J=7 Hz), 8.14 (1H, d, J=7 Hz), 8.60 (1H, s), 8.78 (1H, s).

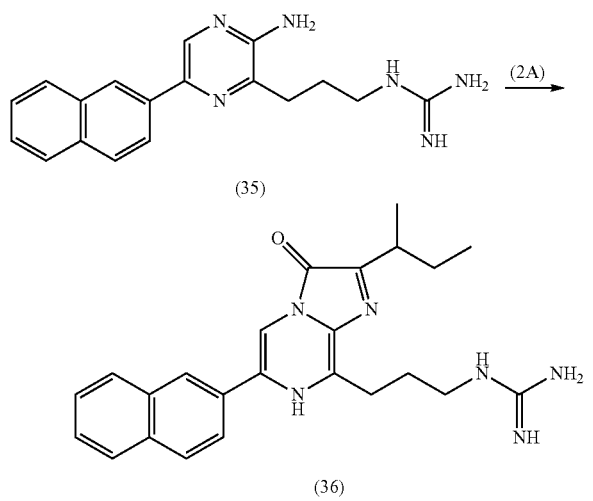

Synthesis of Compound (37)

In a round bottom shaking flask, the compound (16) (10 mg), water (0.1 mL), the compound (33) (0.020 ml), ethanol (0.1 ml) and 49% HBr (0.01 mL) were heated at 100° C. for one hour. The reaction solution was cooled to room temperature, and then concentrated under reduced pressure. A residue was dissolved in ethanol and purified by the LH-20 column to yield the compound (37) (4.4 mg, 30%). $^1$H NMR (500 MHz, CD$_3$OD) 1.83 (3H, d, J=7 Hz), 4.20 (2H, d, J=7 Hz), 4.60 (1H, q, J=7 Hz), 7.18-7.32 (8H, m), 7.42 (1H, d, J=7 Hz), 7.94 (1H, s), 8.07 (1H, d, J=7 Hz), 8.11 (1H, s).

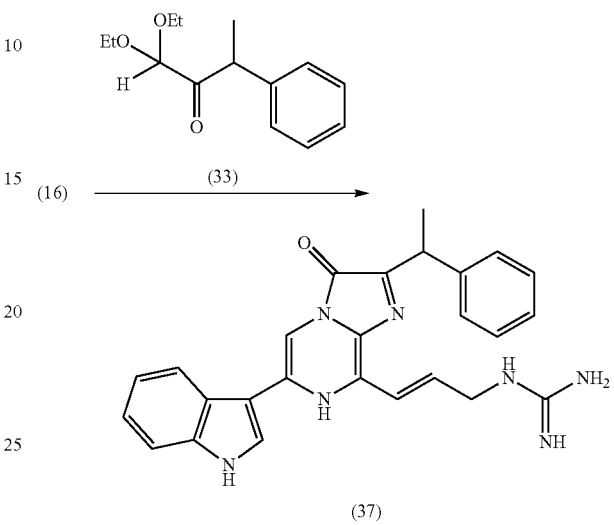

Test Example 1

Measurement of Luminescence Spectra of Marine Ostracod Crustacean Luciferins

Marine ostracod crustacean luciferase (final concentration 100 ng/mL) and marine ostracod crustacean luciferin or the novel marine ostracod crustacean luciferin analog [compound (17)] having olefin group were mixed in 0.1 mL of 50 mM Tris-HCl buffer (pH 7.5), and the luminescence spectrum integrated for 30 seconds was measured. As a result, the luminescence maximum wavelength of the compound (17) was shifted by about 15 nm to the long wavelength side compared with that of native luciferin.

Test Example 2

Measurement of Luminescence Spectra of Marine Ostracod Crustacean Luciferins

Figure 2:
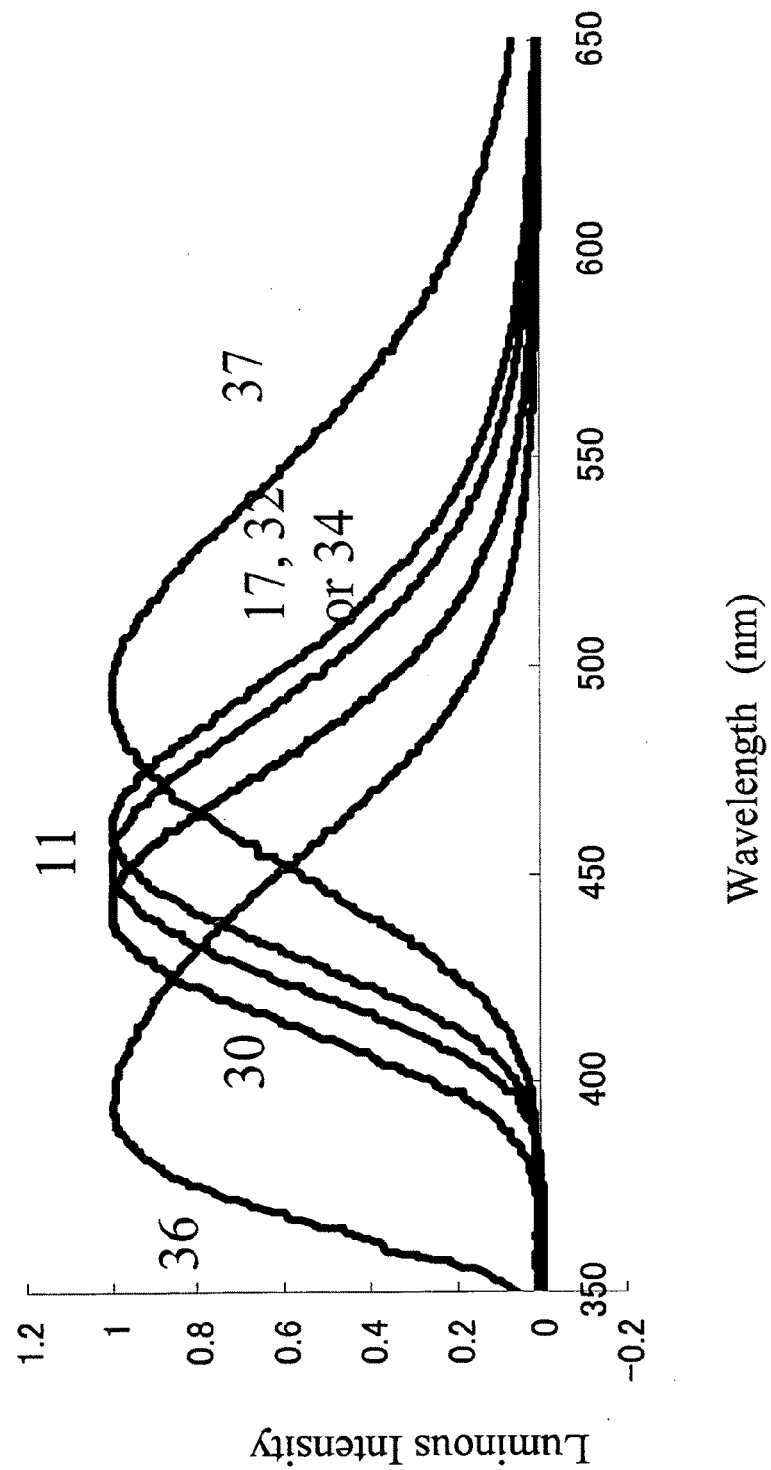
FIG. 2 is a view showing the maximum luminescence wavelength of marine ostracod crustacean luciferin of the present invention.

Marine ostracod crustacean luciferase (final concentration 100 ng/mL) and novel marine ostracod crustacean luciferin analog [compound (30), (32), (34), (36) or (37)] were mixed in 0.1 mL of 50 mM Tris-HCl buffer (pH 7.5), and the luminescence spectrum was measured (FIG. 2).

As a result, it was found that in the case of the compound (30) having benzyl group at position 2 of marine ostracod crustacean luciferin and the compound (36) having sec-butyl group at position 2 and naphthalene at position 6, the biological luminescence wavelength was shifted to the short wavelength whereas in the compounds (32) and (34) having branched benzyl group at position 2, the luminescence wavelength was shifted to the long wavelength, compared with the luminescence wavelength of native luciferin (11). The present invention made it possible to control the luminescence wavelength of marine ostracod crustacean luciferase, which had been conventionally impossible. In particular, in the compound (36), the luminescence maximum wavelength was remarkably shifted to an ultraviolet region (390 nm), and a luminescent color which is different from that in the conventional luminescence system can be exhibited. At the luminescence maximum wavelength of 390 nm, the luminescence is scarcely interfered due to the luminescence by *Renilla* luciferase (blue) and firefly luciferase (yellowish green to red). Thus the luminescence can be measured without using a light filter. A stokes shift between the luminescence maximum wavelength of this compound (36) and the fluorescence maximum wavelength of a green fluorescent protein or a yellow fluorescent protein is large. Thus, if this substrate is used, the interference with the fluorescence maximum wavelength of the fluorescent protein due to the luminescence of marine ostracod crustacean luciferase is lowered. Therefore, this compound is suitable for quantifying the processing of the active peptide from the protein by the fusion body of marine ostracod crustacean luciferase and the fluorescent protein.

Example 9

Marine ostracod crustacean luciferin (final concentration 1 µM) was mixed in 0.1 mL of 100 mM Tris-HCl buffer (pH 7.5) or 0.1 mL of 100 mM Tris-HCl buffer (pH 7.5)/0.3 M NaCl in the presence or absence of 0.3 M sodium ascorbate, and the luminescence value (background) was measured for 10 seconds. Subsequently, marine ostracod crustacean luciferase (final concentration 5 ng/mL) was added, and the luminescence value due to luciferase was measured for 10 seconds. Results are shown in Table 1

In addition, the activity of luciferin after 24 hours at room temperature was measured. The results are shown in Table 2.

As shown in Table 1, in the buffer system containing sodium ascorbate, S/N was improved by at least 16 times or more.

As shown in Table 2, it was found that luciferin was stable at room temperature in 0.1 mL of 100 mM Tris-HCl buffer (pH 7.5) containing 0.3 M sodium ascorbate.

TABLE 1

Measurement values immediately after addition of marine ostracod crustacean luciferin

|  | Luminescence background (count) | Biological luminescence (count) | B/A |
|---|---|---|---|
| 0.1 mL of 100 mM Tris-HCl (pH 7.5) | 2651 | 35961958 | 13565 |
|  | 2605 | 36328201 | 13945 |
| 0.1 mL of 100 mM Tris-HCl (pH 7.5)/0.3M NaCl | 4873 | 38315442 | 7862 |
|  | 4436 | 36058420 | 8128 |
| 0.1 mL of 100 mM Tris-HCl/ 0.3M sodium ascorbate | 161 | 43364001 | 269341 |
|  | 195 | 43814730 | 224690 |

TABLE 2

Measurement values 24 hours after addition of marine ostracod crustacean luciferin

|  | Luminescence background (count) | Biological luminescence (count) | B/A |
|---|---|---|---|
| 0.1 mL of 100 mM Tris-HCl (pH 7.5) | 655 | 212353 | 324 |
|  | 252 | 227062 | 901 |
| 0.1 mL of 100 mM Tris-HCl | 143 | 794325 | 5554 |

TABLE 2-continued

Measurement values 24 hours after addition of marine ostracod crustacean luciferin

|  | Luminescence background (count) | Biological luminescence (count) | B/A |
|---|---|---|---|
| (pH 7.5)/0.3M NaCl | 182 | 783359 | 4304 |
| 0.1 mL of 100 mM Tris-HCl/ 0.3M sodium ascorbate | 204 | 32355906 | 158607 |
|  | 157 | 30478724 | 194132 |

Example 10

Storage of Marine Ostracod Crustacean Luciferin at Room Temperature for More than 24 Hours Marine ostracod crustacean luciferin (final concentration 1 µM) and marine ostracod crustacean luciferase (final concentration 5 ng/mL) were mixed in 100 mM Tris-HCl buffer (pH 7.5) containing 0.3 M sodium ascorbate and 0.02 M sodium sulfite, and the luminescence value due to luciferase was measured for 10 seconds. In addition, the biological luminescence activity of luciferin left stand at room temperature for 24 hours was measured. The results are shown in Table 3.

TABLE 3

|  | Biological luminescence after 0 hour (count) | Biological luminescence after 24 hour (count) |
|---|---|---|
| 0.1 mL of 100 mM Tris-HCl/0.3M sodium ascorbate/0.02M Na$_2$SO$_3$ | 49603053 | 49513568 |

As shown in Table 3, it was found that stability of luciferin at room temperature in 0.1 mL of 100 mM Tris-HCl buffer (pH 7.5) containing 0.3 M sodium ascorbate and 0.02 M Na$_2$SO$_3$ was further enhanced compared with that in the buffer containing 0.3 M sodium ascorbate alone (after 24 hours in Example 9, Table 2).

Example 11

Reduction of BSA Background by Sodium Ascorbate and Sodium Sulfite Which are Antioxidants Marine ostracod crustacean luciferin (final concentration 1 µM) was mixed in 100 mM Tris-HCl buffer/1% BSA (pH 7.5) containing 0.3 M sodium ascorbate, or 0.3 M sodium ascorbate and 0.02 M Na$_2$SO$_3$, or no antioxidant, and the luminescence value was measured for 10 seconds. Subsequently, marine ostracod crustacean luciferase (final concentration 5 ng/mL) was added thereto, and the luminescence value due to luciferase was measured for 10 seconds. The results are shown in Table 4.

TABLE 4

|  | Luminescence background (count) | Biological luminescence (count) | B/A |
|---|---|---|---|
| 0.1 mL of 100 mM Tris-HCl (pH 7.5)/1% BSA | 11216 | 49159227 | 4382 |

TABLE 4-continued

| | Luminescence background (count) | Biological luminescence (count) | B/A |
|---|---|---|---|
| 0.1 mL of 100 mM Tris-HCl (pH 7.5)/1% BSA/0.3M sodium ascorbate | 1590 | 48187479 | 30306 |
| 0.1 mL of 100 mM Tris-HCl/ (pH 7.5)/1% BSA/0.3M sodium ascorbate/0.02M Na$_2$SO$_3$ | 927 | 55916914 | 60320 |

As shown in Table 4, it was found that the luminescence background due to BSA was reduced by about 10 times and the S/N ratio was improved by about 14 times in luciferin in 100 mM Tris-HCl buffer containing 0.3 M sodium ascorbate and 0.02 M Na$_2$SO$_3$.

INDUSTRIAL APPLICABILITY

The marine ostracod crustacean luciferin luminescent substrate of the present invention is practically applicable to dual reporter assay methods using marine ostracod crustacean luciferase and marine ostracod crustacean luciferin analog (having the different luminescence wavelength).

Specifically,

1. A system in which two gene transcription activities are measured by extracellularly secreted proteins using two marine ostracod crustacean luciferases having the luminescence maximum wavelength of 390 to 620 nm and emitting the light whose luminescence wavelength does not depend on the measurement condition and a marine ostracod crustacean luciferase/fluorescent protein fusion body gene.

Figure 3A:
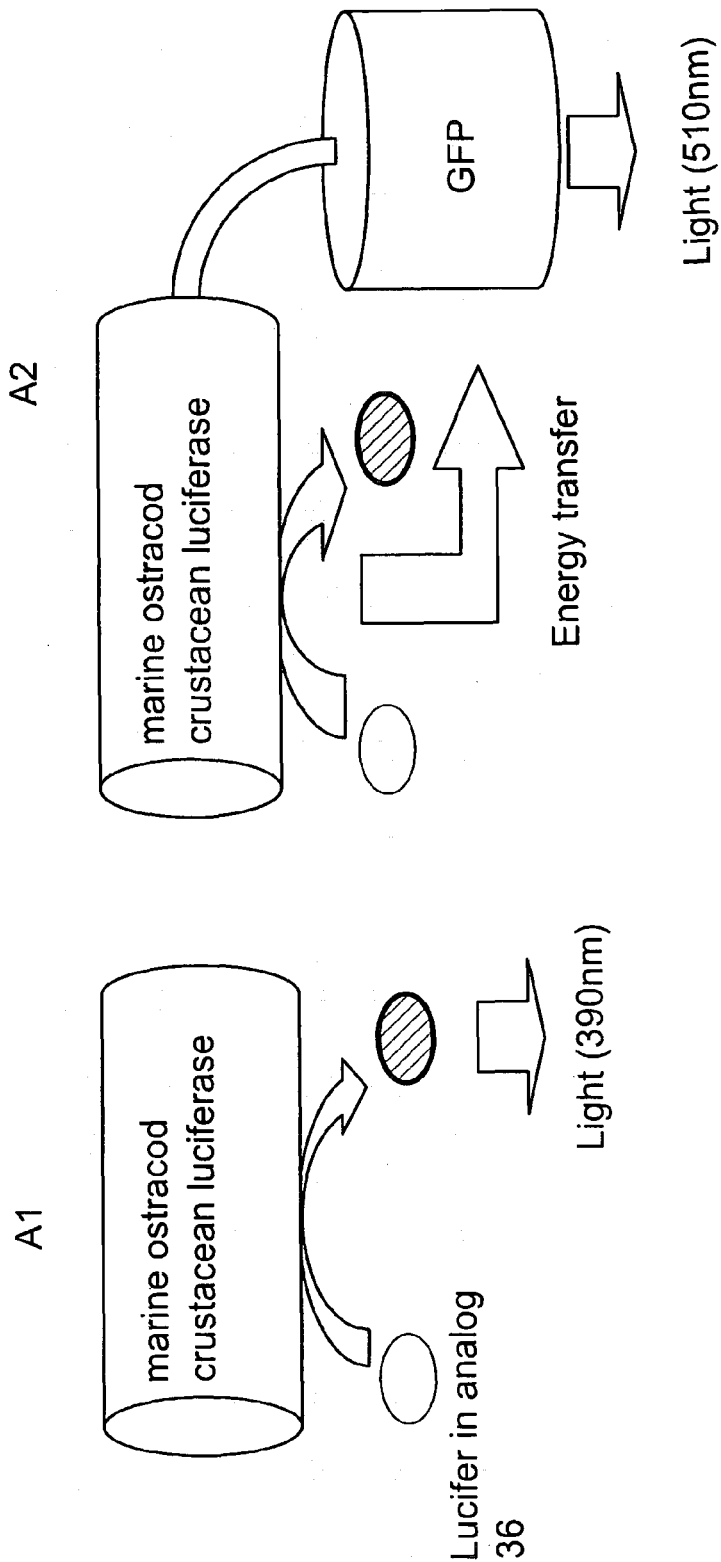
FIG. 3 is a view showing application examples of a marine ostracod crustacean luciferin derivative of the present invention. 3A: Luminescence principles of marine ostracod crustacean luciferase and a fusion body of marine ostracod crustacean luciferase/a fluorescent protein (A1 represents marine ostracod crustacean luciferase/luciferin analog 36, and A2 represents marine ostracod crustacean luciferase/green fluorescent protein fusion body/luciferin analog 36). 3B: Dual reporter assay (gene construct for measuring the gene transcription activity of two promoter sequences A and B). 3C: Change of luminescence spectra by the dual reporter assay [I: Spectrum generated by activating the promoter A (expression of only the promoter A); II: spectrum obtained before activating the promoter B; III: spectrum after activating the promoter B; ↑: increase of relative luminescence activity (B/A) together with activation of the promoter B).

2. A luminescence reaction in which the luminescence maximum wavelength is 390 to 520 nm by the reaction of marine ostracod crustacean luciferase and the marine ostracod crustacean luciferin analog. In the marine ostracod crustacean luciferin analog 36, the maximum luminescence wavelength is about 390 nm (FIG. 3A).

3. A luminescence reaction in which the luminescence maximum wavelength is 500 to 620 nm by the reaction of the marine ostracod crustacean luciferase/fluorescent protein fusion body and the marine ostracod crustacean luciferin analog. For example, in marine ostracod crustacean luciferase/GFP, the wavelength is about 510 nm (FIG. 3A).

4. In the combination of the above 2 and 3, it is desirable that the maximum luminescence wavelengths are separated by 100 nm or more, but color segmentation is possible in separation of 30 nm. Thus, the dual reporter assay is performed using that combination.

Figure 3B:
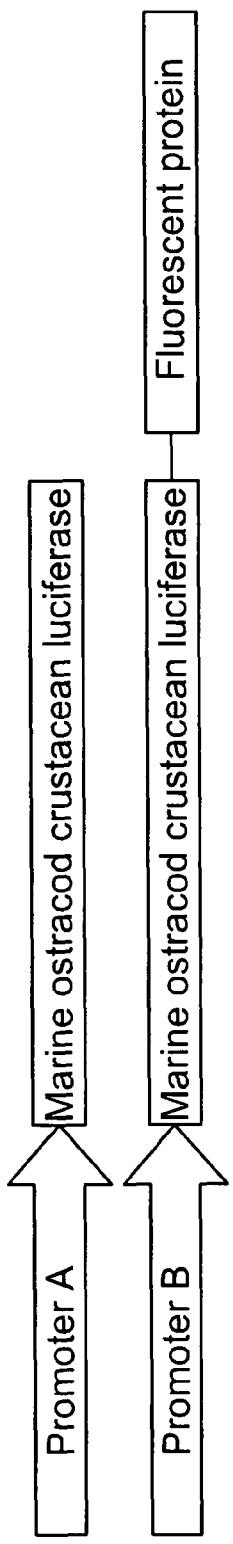
Figure 3C:
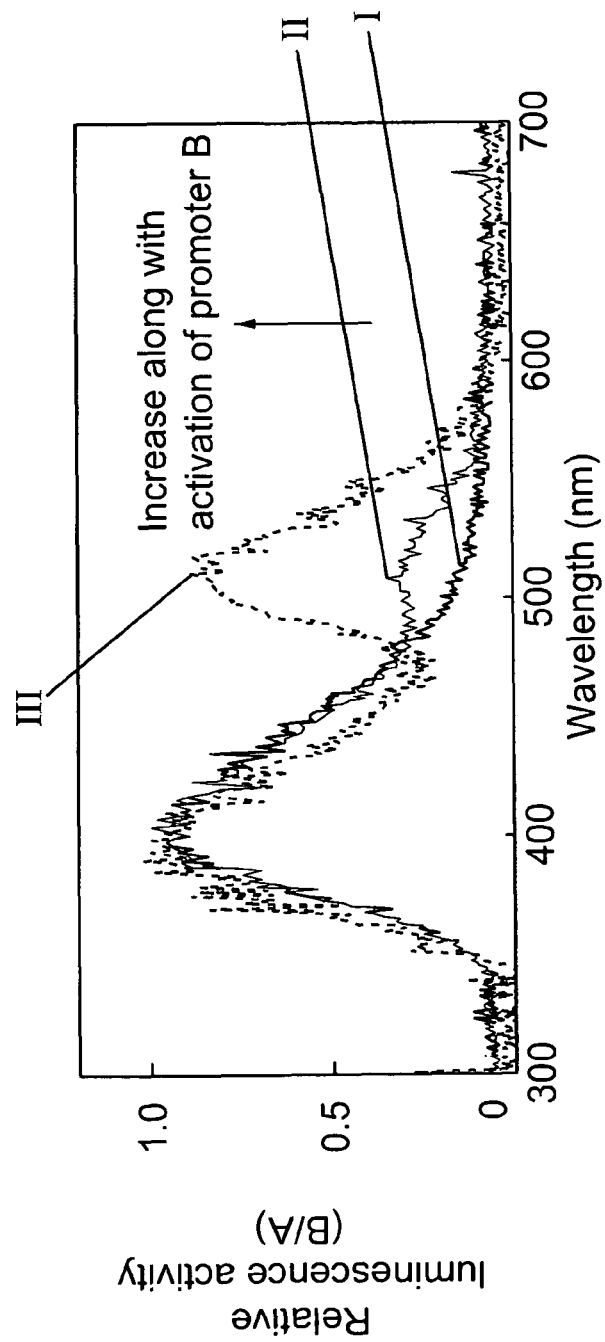

5. A promoter A is inserted upstream of a marine ostracod crustacean luciferase gene and a promoter B is inserted upstream of the marine ostracod crustacean luciferase/fluorescent protein fusion body gene (FIG. 3B). Cells are transfected with these two gene constructs, and cultured for a certain time period after the transfection. Subsequently, the marine ostracod crustacean luciferin analog is directly added to a collected culture medium or a culture plate, the luminescence is segmented by a color filter and two luminescence quantities are measured to determine activity amounts of the promoters A and B (Since it is not necessary to lyse the cells, the gene transcription activity can be measured in the living cells) (FIG. 3C). When only the promoter A is activated, only the luminescence at the maximum luminescence wavelength of 390 nm is observed. Along with activating the promoter B, a peak around 510 nm is observed, and this is increased. The luminescence spectra can be easily separated by the filter.

The invention claimed is:

1. A marine ostracod crustacean luciferin stabilization composition comprising marine ostracod crustacean luciferin or an analog thereof, an ascorbic acid or a salt thereof, and a sulfite salt.

2. A method for storing marine ostracod crustacean luciferin or an analog thereof characterized by storing marine ostracod crustacean luciferin or the analog thereof in the presence of an ascorbic acid or a salt thereof, and a sulfite salt.

3. A kit for using in a marine ostracod crustacean biological luminescence system, comprising marine ostracod crustacean luciferin or an analog thereof, an ascorbic acid or a salt thereof, and a sulfite salt.

4. A method for reducing a background in a marine ostracod crustacean biological luminescence system comprising administering an ascorbic acid or a salt thereof and a sulfite salt to the marine ostracod crustacean biological luminescence system.

5. A method for measuring biological luminescence in a marine ostracod crustacean system characterized in that the biological luminescence is measured in the presence of an ascorbic acid or a salt thereof and a sulfite salt in a biological luminescence measurement system of marine ostracod crustacean luciferase and marine ostracod crustacean luciferin or an analog thereof.

* * * * *